US012478125B2

(12) United States Patent
Henshaw

(10) Patent No.: US 12,478,125 B2
(45) Date of Patent: Nov. 25, 2025

(54) FACE SHIELD WITH POWERED AIR PURIFYING RESPIRATOR AND METHODS OF USE

(71) Applicant: Robert J. Henshaw, Newnan, GA (US)

(72) Inventor: Robert J. Henshaw, Newnan, GA (US)

( * ) Notice: Subject to any disclaimer, the term of this patent is extended or adjusted under 35 U.S.C. 154(b) by 1093 days.

(21) Appl. No.: 17/489,623

(22) Filed: Sep. 29, 2021

(65) Prior Publication Data

US 2022/0095736 A1 Mar. 31, 2022

Related U.S. Application Data

(60) Provisional application No. 63/084,895, filed on Sep. 29, 2020.

(51) Int. Cl.

| | |
|---|---|
| ***A42B 3/22*** | (2006.01) |
| ***A42B 3/28*** | (2006.01) |
| ***A61F 9/06*** | (2006.01) |
| ***A62B 18/04*** | (2006.01) |

(52) U.S. Cl.

CPC ............ *A42B 3/225* (2013.01); *A62B 18/045* (2013.01); *A42B 3/288* (2013.01); *A61F 9/068* (2013.01)

(58) Field of Classification Search

CPC ......... A42B 3/225; A42B 3/286; A42B 3/288; A62B 18/02; A62B 18/025; A62B 18/045; A62B 18/08; A61F 9/068

See application file for complete search history.

(56) References Cited

U.S. PATENT DOCUMENTS 3,822,698 A 7/1974 Guy
5,054,479 A * 10/1991 Yelland .................... A61F 9/02 2/9
5,054,480 A 10/1991 Bare
5,104,430 A 4/1992 Her-Mou
5,113,853 A * 5/1992 Dickey ................ A62B 18/045 128/201.24

(Continued)

FOREIGN PATENT DOCUMENTS

WO 2021089626 5/2021

OTHER PUBLICATIONS

Thanko Pollen Blocker 2, Hay fever allergy protective wear, Japan Trend Shop, https://www.japantrendshop.com/thanko-pollen-blocker-2-p-4733.html.

(Continued)

*Primary Examiner* — Valerie L Woodward

(74) *Attorney, Agent, or Firm* — Mathew L. Grell, Esq.; Grell & Watson Patent Attorneys LLC

(57) ABSTRACT

Air purifying respirator for user's having a face shield configured to shield the user's face from splatter, a head strap configured to encircle at least a portion of the users head, said head strap configured to support the face shield, at least one fan, and a fan housing positioned proximate an upper edge of the face shield, said fan housing configured to support said fan, a filter media positioned on an outer perimeter flange of the fan housing to maximizing a surface area of said filter media, a face shroud connected to a perimeter of the face shield, the face shroud configured to provide a seal between the face shield and the user's face and thus, to facilitate pulling the air through the filter media, and the fan pushes the filtered air from said fan housing to the user between said face shield and the user's face.

24 Claims, 23 Drawing Sheets

(56) References Cited

U.S. PATENT DOCUMENTS

| | | | |
|---|---|---|---|
| 5,125,402 A | 6/1992 | Greenough | |
| 5,291,880 A | 3/1994 | Almovist et al. | |
| 5,561,862 A | 10/1996 | Flores | |
| 5,577,495 A | 11/1996 | Murphy | |
| 5,592,936 A | 1/1997 | Thomas | |
| 5,673,431 A * | 10/1997 | Batty | A61F 9/027 2/9 |
| 5,711,033 A | 1/1998 | Green | |
| 6,374,823 B1 | 4/2002 | Hajianpour | |
| 6,393,617 B1 | 5/2002 | Paris | |
| 6,481,019 B2 | 11/2002 | Diaz | |
| 6,619,286 B2 | 9/2003 | Patel | |
| 6,622,311 B2 | 9/2003 | Diaz | |
| 6,973,677 B2 | 12/2005 | Diaz | |
| 8,756,715 B1 | 6/2014 | Moffitt | |
| 8,916,224 B2 | 12/2014 | Karwowski | |
| 8,955,168 B2 | 2/2015 | Manzella | |
| 9,241,529 B1 | 1/2016 | Danelski | |
| 10,278,442 B2 | 5/2019 | Wang | |
| 10,709,194 B2 | 7/2020 | Johnstone | |
| 2013/0014751 A1 | 1/2013 | Ausen | |
| 2016/0030779 A1* | 2/2016 | Twu | A62B 18/02 128/202.13 |
| 2018/0242679 A1* | 8/2018 | Johnstone | A42B 3/288 |
| 2019/0258749 A1* | 8/2019 | Ho | G06F 30/00 |
| 2021/0331000 A1* | 10/2021 | Gilner | A62B 18/086 |

OTHER PUBLICATIONS

International Search Report and Written Opinion issued in corresponding International Application No. PCT/US21/52733.

* cited by examiner

FACE SHIELD WITH POWERED AIR PURIFYING RESPIRATOR AND METHODS OF USE

CROSS-REFERENCE TO RELATED APPLICATIONS

To the full extent permitted by law, the present United States Non-Provisional patent application hereby claims priority to and the full benefit of U.S. Provisional Application No. 63/084,895, filed on Sep. 29, 2020, entitled "Face Shield with Powered Air Purifying Respirator and Methods of Use", which is incorporated by reference herein in its entirety.

FIELD OF THE DISCLOSURE

The present disclosure is directed to an air filter and face mask. More specifically, the present disclosure is directed to face shield with powered air purifying respirator.

BACKGROUND

The air we breathe contains dust, dirt, pollen, noxious fumes, bacteria, viruses, and fungus and other airborne particulate. In the age of COVID-19 various approaches or form factors have been utilized to prevent the spread of the virus from person to person, such as wearing a filter material over their nose and mouth and/or a face shield, social distancing in public, and sheltering in place. However, some workers in categories classified as critical are still required to perform their duties and are unable to perform such tasks and maintain social distancing.

One approach to prevent the spreads of a flu virus has been the use of N95 respirators, surgical masks, and other face masks that attempt to create a physical barrier between the mouth and nose of the wearer and potential contaminants in the immediate environment. N95 respirators are regulated under product code MSH as class II medical devices exempt from 510(k) premarket notification unless respirator is labeled or otherwise represented as filtering specific amounts of viruses or bacteria, reducing the amount of and/or killing viruses, bacteria. Thus, if unlabeled as filtering specific amounts of viruses or bacteria, these respirators can stop large-particle droplets, splashes, sprays, or splatter that may contain germs (viruses and bacteria) from entering the wearers nose or mouth. One disadvantage or drawback to these approaches is that these respirators have difficulty forming a seal around the perimeter of the respirator and the users face. Another disadvantage or drawback to these approaches is that these respirators do not filter or block very small particles in the air that may contain germs (viruses and bacteria) from entering the wearers nose or mouth. Still another disadvantage or drawback to these approaches is that these respirators are made in different thicknesses which also may also affect how easily you can breathe through the material.

One approach to prevent the spreads of a flu virus has been the use of face shields that attempt to create a physical barrier between the eyes, mouth, and nose of the wearer to stop large-particle droplets, splashes, sprays, or splatter that may contain germs (viruses and bacteria) from entering the wearers eyes, nose, or mouth. One disadvantage or drawback to these approaches is that these face shields have difficulty protecting side or back splashes, sprays, or splatter.

Therefore, it is readily apparent that there is a recognizable unmet need for a face shield with powered air purifying respirator and methods of use that may be configured to address at least some aspects of the problems discussed above common to prevent the spread of the virus and other contaminating particulates via a two tiered protection device to block small and large-particle droplets, splashes, sprays, or splatter that may contain germs (viruses and bacteria) from entering the wearers eyes, nose, or mouth.

SUMMARY

Briefly described, in an example embodiment, the present disclosure may overcome the above-mentioned disadvantages and may meet the recognized need for a face shield with powered air purifying respirator and methods of use, including an air purifying respirator for a user's head having a face, a forehead and a back head with a face shield, the face shield configured to shield the user's face, a face shroud connected to a perimeter of the face shield, the face shroud configured to provide a seal between the face shield and the user's face, a head strap configured to encircle at least a portion of the users head, the head strap configured to support the face shield, at least one fan, a fan housing positioned proximate an upper edge of the face shield, the fan housing configured to support the fan, a filter chamber connected to said fan housing, the filter chamber configured to supports a filter media positioned proximate an exterior environment.

Accordingly, in one aspect, the present disclosure may be configured to provide filtered air to the wearer via a battery powered, motorized fan and filter system. The system consists of a clear face shield, air filtering media, filter media housing, a motorized fan, head strap and battery.

Accordingly, in another aspect, the present disclosure may be configured where air is drawn through the filter media located on the outer brow area of the face shield via a motorized fan mounted between the filter media and above the plane of the eye brow of the wearer.

Accordingly, in another aspect, the present disclosure may be configured with a filter media and a fan capable of drawing air through the filter media capable of filtering smoke or plumes, filtering small particulate, filtering specific amounts of viruses or bacteria, reducing the amount of and/or killing viruses, bacteria, or fungi, or affecting allergenicity (purifying). Moreover, filter media may contain a coating technology to reduce and or kill microorganisms.

Accordingly, in another aspect, the present disclosure may be configured where filtered air is blown into the space between the wearers face and the interior of the face shield. This produces a positive pressure condition which prevents the wearer from being exposed to the potentially contaminated ambient environment the wearer is in.

Accordingly, in another aspect, the present disclosure may be configured having a face shroud connected to a perimeter of the face shield, the face shroud configured to provide a seal between the face shield and the user's face forming a seal around the perimeter of the respirator and the users face to block small and large-particle droplets, splashes, sprays, or splatter that may contain germs (viruses and bacteria) from entering the wearers eyes, nose, or mouth.

Accordingly, in another aspect, the present disclosure may be configured where this barrier allows air to vent through the shroud but can serve to filter the wearer's exhalation and thus potential pathogens before exhausting into the environment. In applications where exhalation filtering isn't required this shroud can also protect the wearer from flying dust and debris which in some cases could overpower the positive pressure envelope as well as protecting side or back splashes, sprays, or splatter.

Accordingly, in another aspect, the present disclosure may include any and all dimensional relationships, to include variations in size, material, shape, form, position, function and manner of operation, assembly and use, are intended to be encompassed by the present disclosure.

In another exemplary embodiment of the air purifying respirator for a user's head having a face and a forehead to deliver a filtered air and provide shield to a splatter, including a face shield, said face shield configured to shield the user's face from the splatter, a powered air purifying system, said system having at least one fan to provide a positive air pressure between the face shield and the user's face, a fan housing positioned proximate an upper edge of the face shield, the fan housing having a fan support, a forehead support wall, an outer perimeter flange, configured to support the fan internally therein and to enable efficient movement of the air, a head strap attached to the fan housing, the head strap configured to encircle at least a portion of the users head, the head strap configured to support the fan housing, and a filter media positioned on an outer perimeter flange of the fan housing to maximizing a surface area of the filter media, wherein the fan pulls the air through the filter media, and the fan pushes the filtered air from the fan housing into the user between the face shield and the user's face.

In another exemplary embodiment of the air purifying respirator for a user's head having a face and a forehead to deliver a filtered air and provide shield to a splatter, including a hard hat having a visor, a powered air purifying system positioned proximate the visor, the system having a face shield, the face shield configured to shield the user's face from the splatter, at least one fan to provide a positive air pressure between the face shield and the user's face, a fan housing positioned proximate an upper edge of the face shield, the fan housing having a fan support, a forehead support wall, an outer perimeter flange, configured to support the fan internally therein and to enable efficient movement of the air, and a filter media positioned on an outer perimeter flange of the fan housing to maximizing a surface area of the filter media, wherein the fan pulls the air through the filter media, and the fan pushes the filtered air from the fan housing into the user between the face shield and the user's face.

A feature of the present disclosure may include a facemask with a removeable external air filter and built-in powered air blower which removes contaminants from the surrounding air and continuously delivers the purified air under positive pressure to an area between the wearers face and a transparent or see through face shield.

A feature of the present disclosure may include a fan to draw air through an external filter enables smaller porosity and pore connectivity filter material with nano- and micro-fiber layers to be utilized. Contrasted with wearers lung capacity to pull air through a filter material, such as N95 masks which have pores from 10-65 micrometers. Masks, surgical masks, and N95 masks average 47, 33, 30 micro meters average pore diameter. An effective filter material must be capable of handling microscale droplets which evaporate into nanoscale aerosols carrying germs (viruses and bacteria). Powered air purifying respirators (PAPR) having a fan provide wearers generally a higher level of protection than non-powered filtering masks from air-borne pathogens, materials and fumes.

A feature of the present disclosure may include an exterior or outer filter in relation to the fan and mask body (rather than in interior filter which contaminates the internal passageways prior to the filter) for ease of replacement as well as an increased filter surface area to provide adequate air flow through the filter material to provide a positive air pressure proximate wearers eyes, nose, and mouth.

A feature of the present disclosure may include to provide a portable self-contained powered air purifying respirator and face shield which provides filtered air to wearer's face area and excludes unpurified air, and protects wearer' eyes, nose, and mouth A feature of the present disclosure may include a face shroud connected to a perimeter of the face shield, the face shroud configured to provide a seal between the face shield and the user's face to block water droplets expelled into the environment by coughs and sneezes.

A feature of the present disclosure may include comfortability to the wearer rather than non-powered respirators. Moreover, PAPRs also allow third parties such as associates and patients to see the wearer's mouth which aids in communication and reduces miscommunication especially in critical decision making environments.

A feature of the present disclosure may include quick exchange or replacement of filter media since the filter material is on the exterior of the mask housing enabling use of a variety of filter material with nano- and micro-fiber layers to be utilize and enables frequent rotation of filter material always insuring a dry and bacteria, virus, and particle free filter material.

A feature of the present disclosure may include optimizing the placement of the powered fan and filter assembly directly in front of the wearer's forehead which eliminates the need for complex ducting and the associated head gear.

A feature of the present disclosure may include a filter media and powered fan assembly which minimizes the number of parts which both reduces the weight and bulk of this new PAPR.

A feature of the present disclosure may include a filter media configured as two dimensional flat shape which may be fitted to the outer surface of the filter cowl and perimeter flange providing a large surface area of filter media for filtering while not requiring any complex manufacturing forming operations as compared with other more complex filters, such as pleated media fitted into a cartridge. Thus, this filter design reduces the supply constraint issues, especially during high demand cycles during a pandemic and reduces the overall cost of the filter material and allows the greatest amount of flexibility in utilizing alternative filter media in emergency situations.

A feature of the present disclosure may include a filter media configured having a removable adhesive backer to adhere and seal filter media to outer surface of the filter cowl and perimeter flange.

A feature of the present disclosure may include mounting the system to a helmet such as a construction hard hat, welding helmet, etc.

A feature of the present disclosure may include a respirator system may be utilized in other industries or integrated with other face shields to provide air movement functionality therein.

A feature of the present disclosure may include used with or without a breathable elastic face shroud which forms a barrier bridging between the wearers face and the face shield.

A feature of the present disclosure may include being lighter and more economical to produce than the current state of the art in PAPRs.

A feature of the present disclosure may include no requirement of a conduit to move air from the fan to the wearer's face.

A feature of the present disclosure may include the efficient design of fan support, forehead support wall, and outer perimeter flange to provide a fan plenum box for motorized fan to enable efficient movement of air and to provide a large surface are for filter media.

These and other features of the face shield with powered air purifying respirator and methods of use will become more apparent to one skilled in the art from the prior Summary and following Brief Description of the Drawings, Detailed Description of exemplary embodiments thereof, and Claims when read in light of the accompanying Drawings or Figures.

BRIEF DESCRIPTION OF THE DRAWINGS

The present a face shield with powered air purifying respirator and methods of use will be better understood by reading the Detailed Description of the Preferred and Selected Alternate Embodiments with reference to the accompanying drawing Figures, in which like reference numerals denote similar structure and refer to like elements throughout, and in which.

Figure 1:
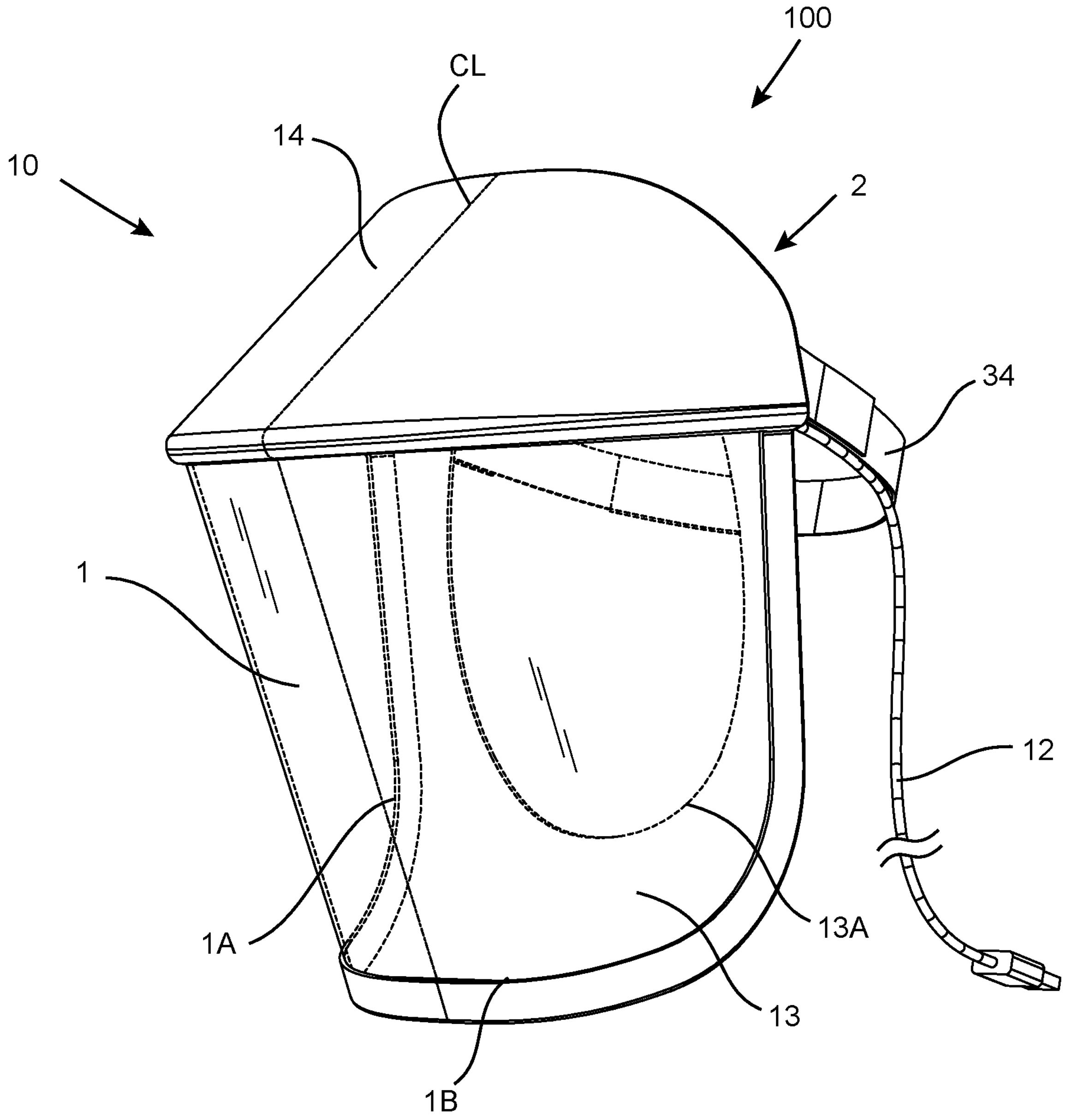
FIG. 1 is a perspective side view of the face shield with powered air purifying respirator system according to select embodiments of the instant disclosure.
Figure 2:
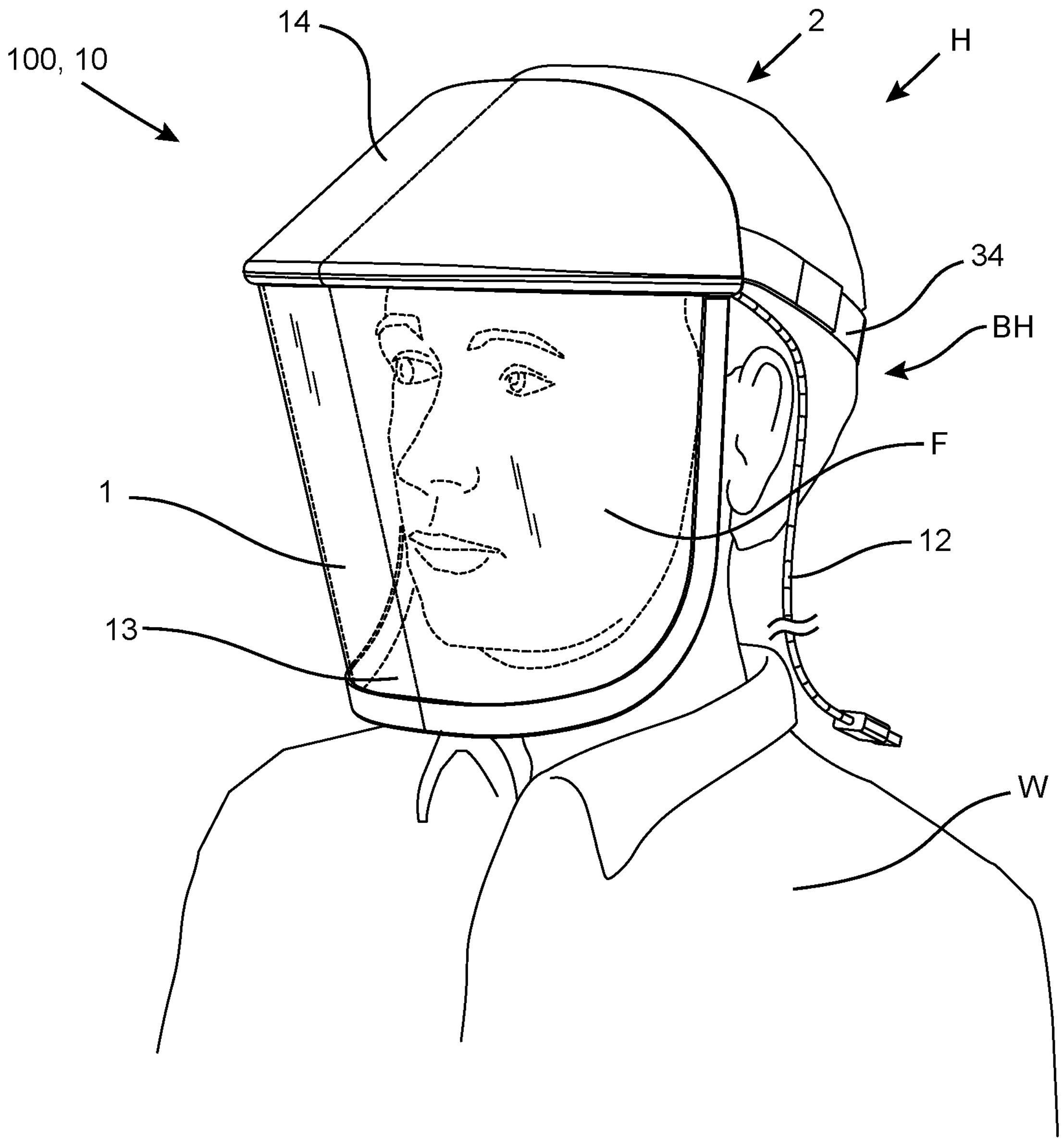
FIG. 2 is a perspective side view of the face shield with powered air purifying respirator system according to select embodiments of the instant disclosure, shown in use and worn by a wearer or user.
Figure 3:
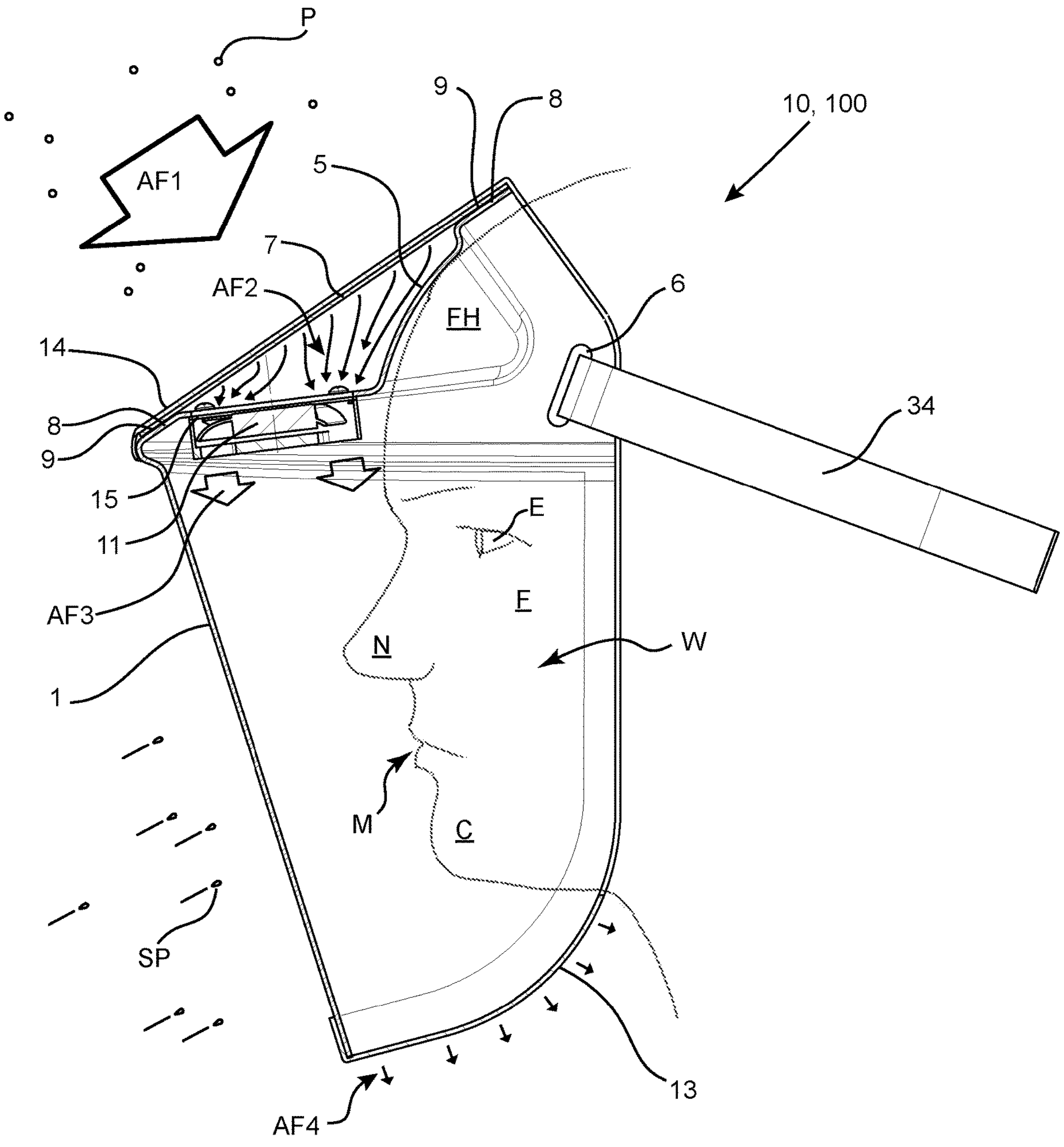
FIG. 3 is a partial cross-sectional side view of the face shield with powered air purifying respirator system according to select embodiments of the instant disclosure, showing air flow patterns through the filter material, fan, and into the area between the face shield and wearer's face.
Figure 4:
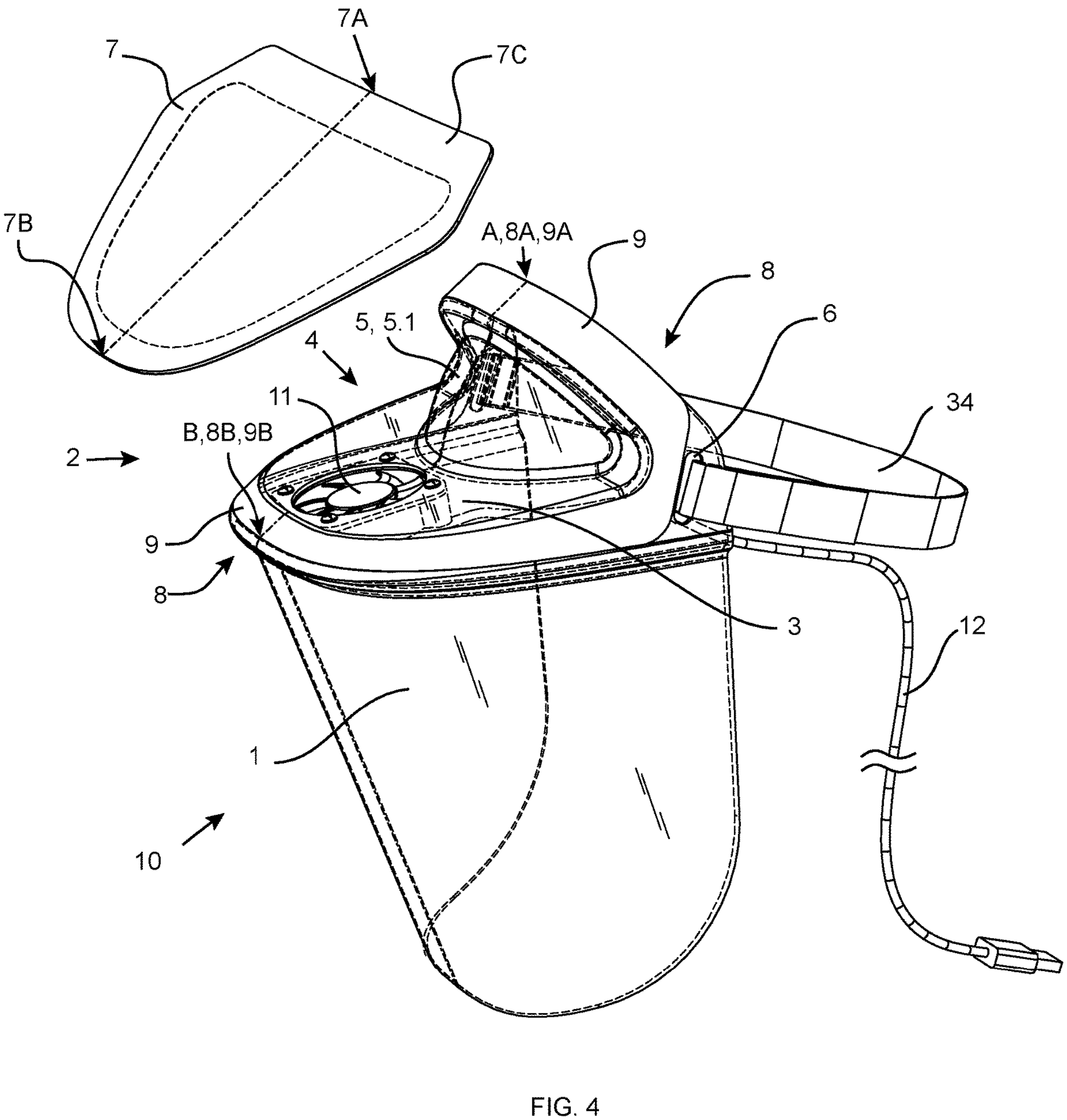
FIG. 4 is a top perspective view of the face shield with powered air purifying respirator system according to select embodiments of the instant disclosure, showing external filter material removed exposing the internal fan chamber and fan assembly.
Figure 5:
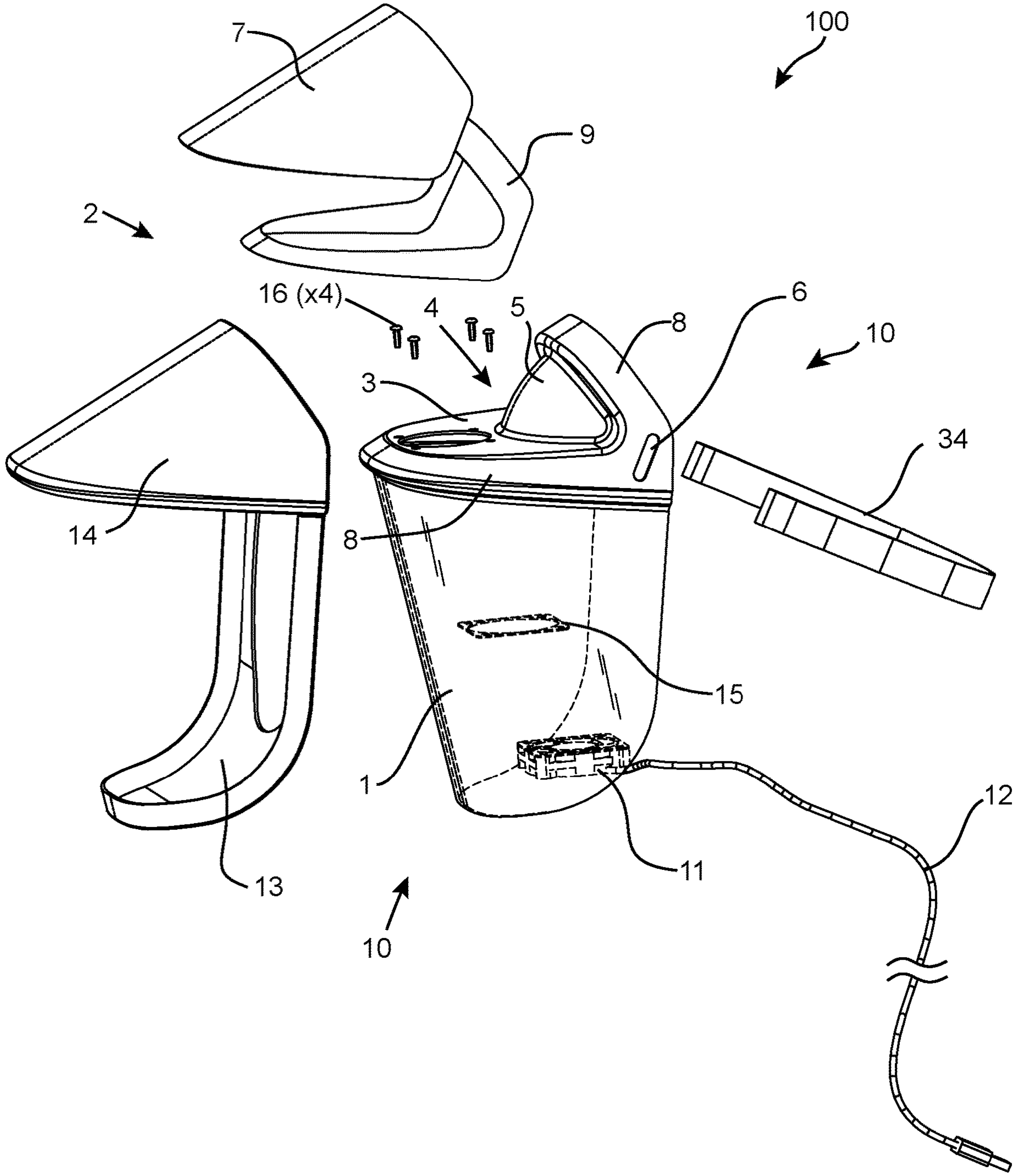
FIG. 5 is an exploded perspective view of the face shield with powered air purifying respirator system according to select embodiments of the instant disclosure.
Figure 6:
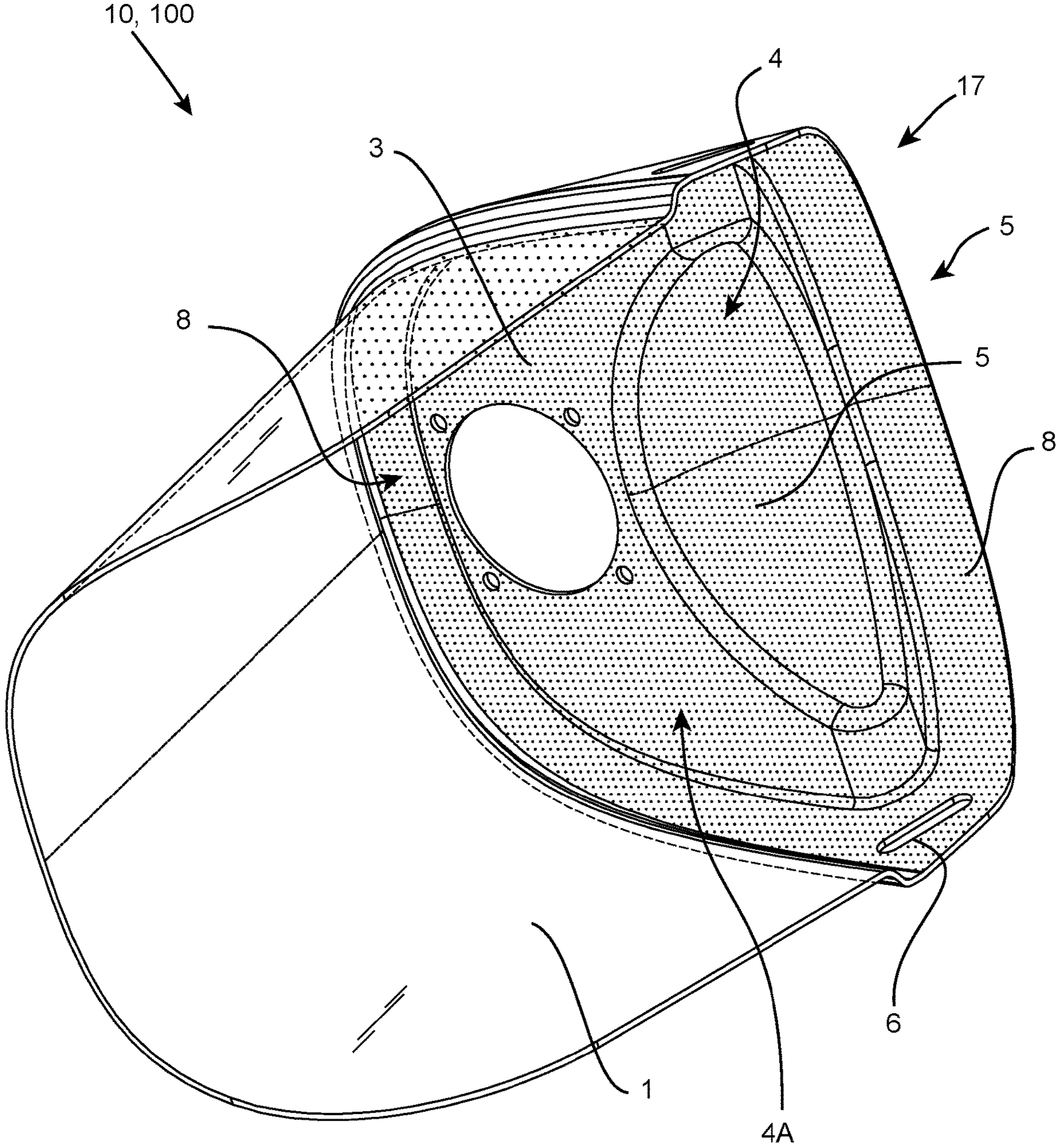
FIG. 6 is a bottom perspective view of the face shield of powered air purifying respirator system according to select embodiments of the instant disclosure, showing face shield, fan housing, and visor.
Figure 7:
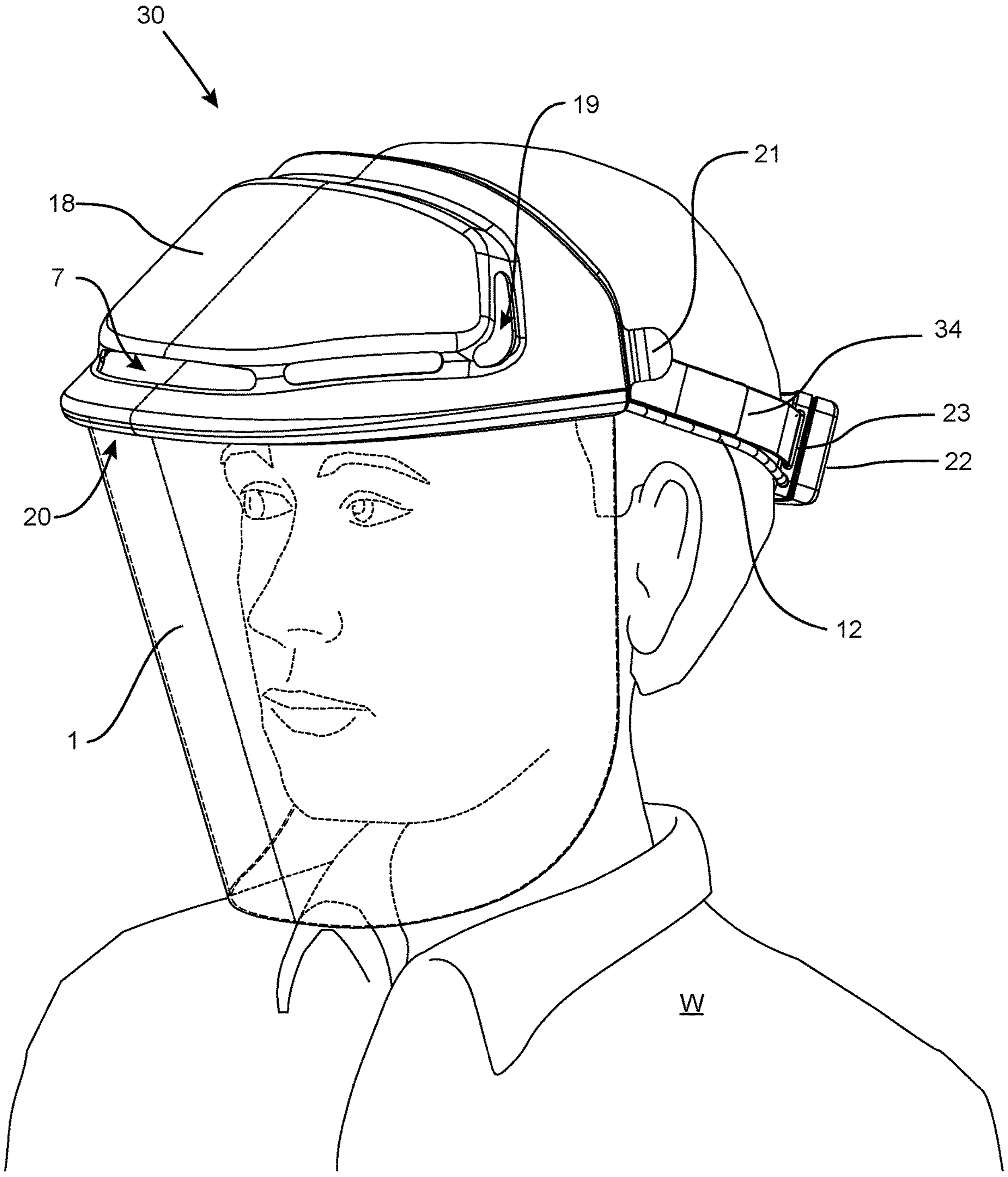
FIG. 7 is a perspective side view of the powered air purifying respirator system according to select embodiments of the instant disclosure, shown in use and worn by a wearer or user with the addition of filter media vented cover.
Figure 8:
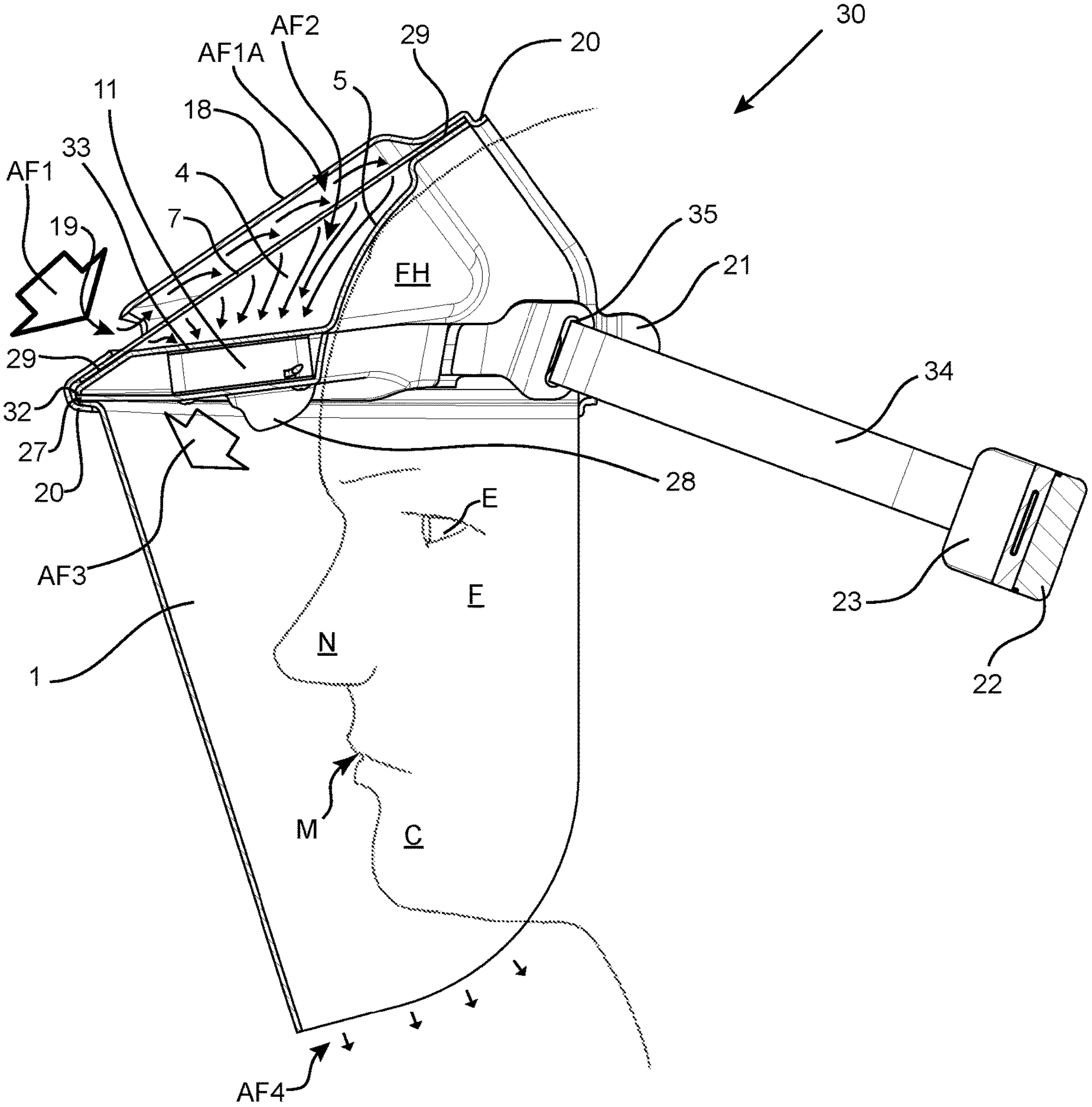
FIG. 8 is a partial cross-sectional side view of the powered air purifying respirator system according to select embodiments of the instant disclosure, showing air flow patterns through the vented cover, filter material, fan, and into the area between the face shield and wearer's face.
Figure 9:
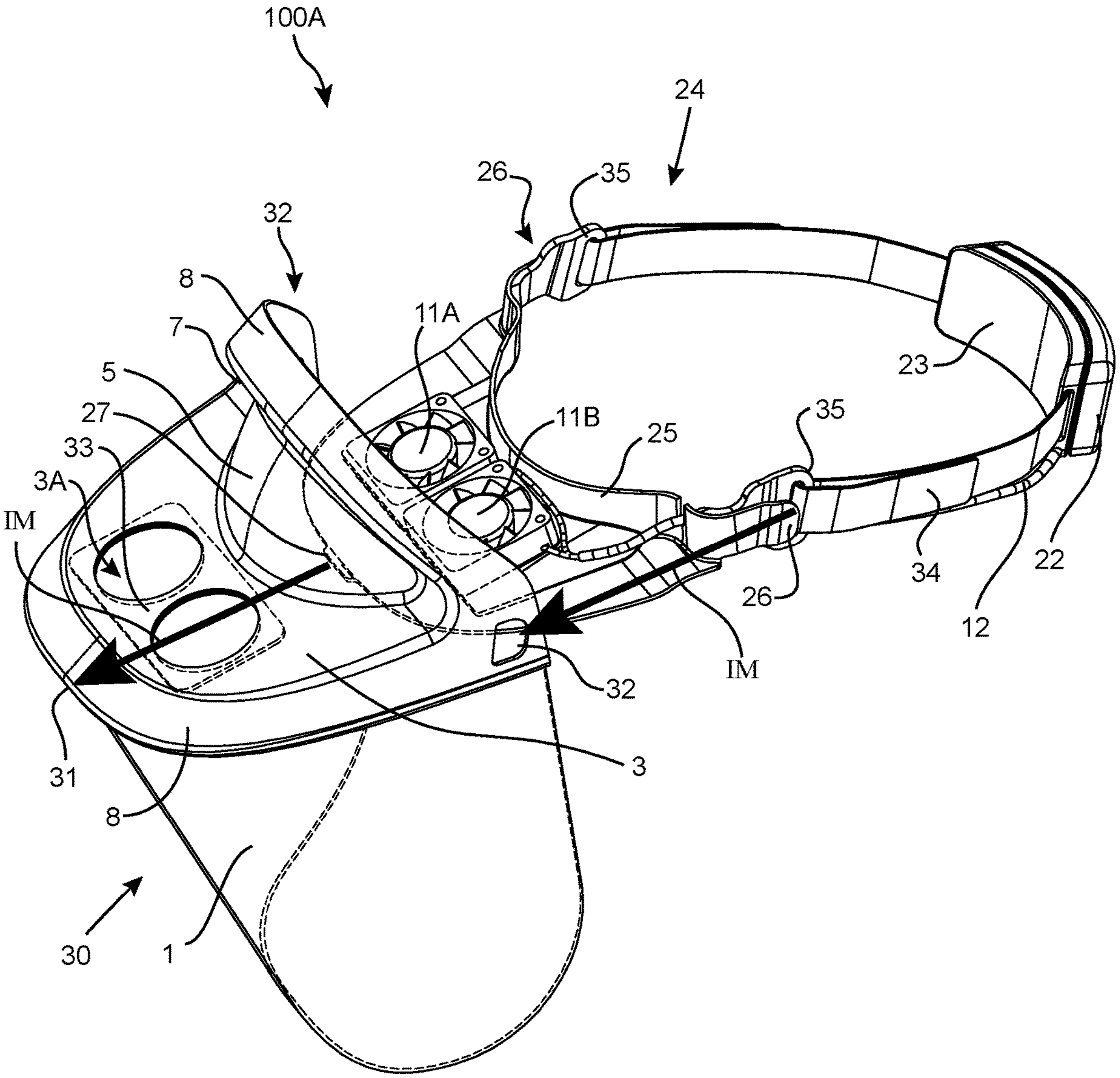
FIG. 9 is an exploded perspective view of the face shield, primary structure, fan assembly and headgear of powered air purifying respirator system according to select embodiments of the instant disclosure.
Figure 10:
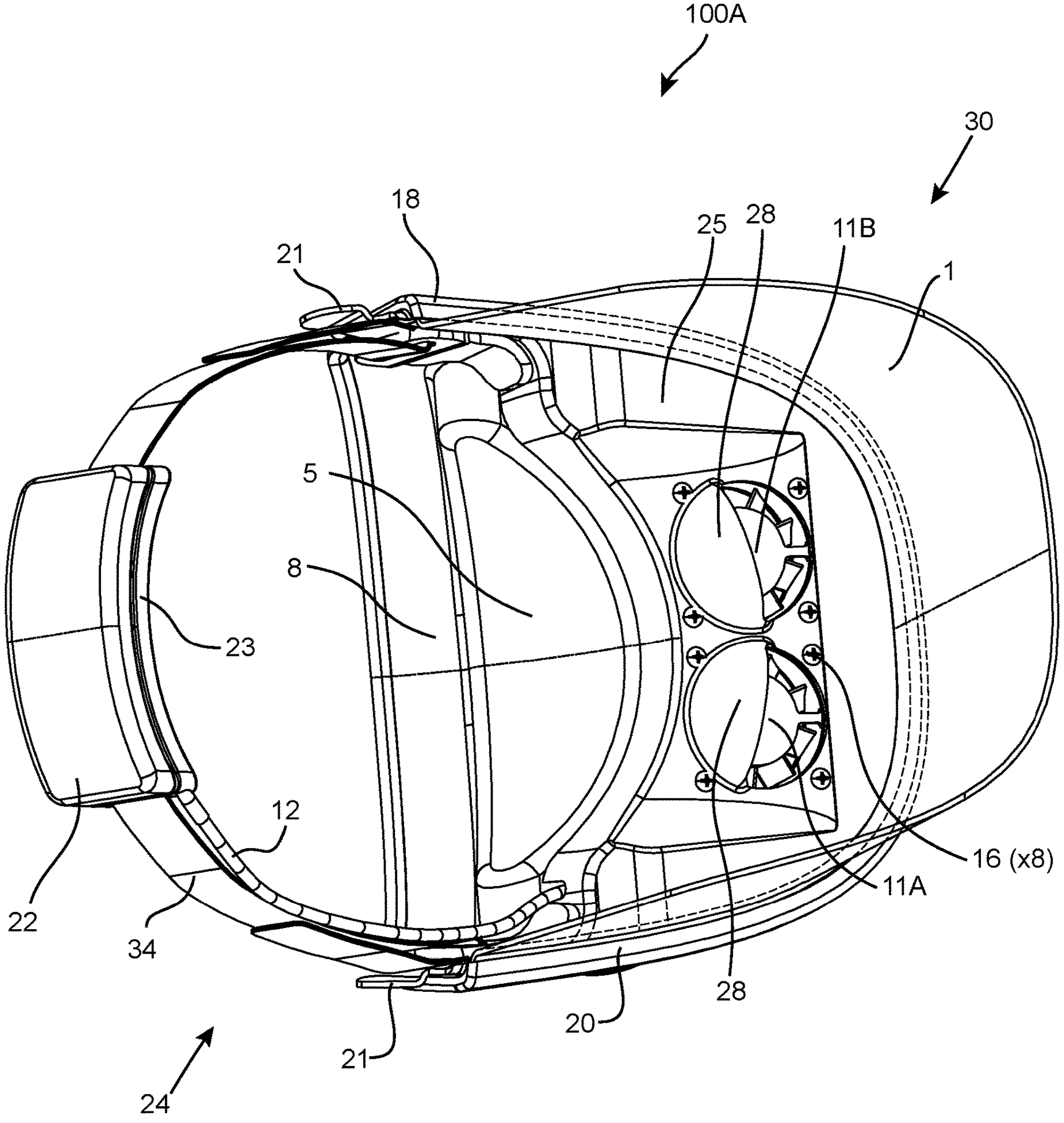
FIG. 10 is a bottom perspective view of the face shield, primary structure, fan assembly and head gear of powered air purifying respirator system according to select embodiments of the instant disclosure, showing the fan diffuser frame and fan diffuser.

It is to be noted that the drawings presented are intended solely for the purpose of illustration and that they are, therefore, neither desired nor intended to limit the disclosure to any or all of the exact details of construction shown, except insofar as they may be deemed essential to the claimed disclosure.

DETAILED DESCRIPTION

In describing the exemplary embodiments of the present disclosure, as illustrated in the figures, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples, and are merely examples among other possible examples.

With respect to the above description then, it is to be realized that the optimum dimensional relationships, to include variations in size, materials, shape, form, position, movement mechanisms, function and manner of operation, assembly and use, are intended to be encompassed by the present disclosure.

Referring now to FIGS. 1-8, by way of example, and not limitation, there is illustrated an example embodiment of face shield with powered air purifying respirator system 100, according to this select embodiment. Face shield with powered air purifying respirator system 100 may be utilized as an air purifying respirator for a user or wearer W head H having face F, forehead FH and back of head BH with face shield 1 provide the functionality of filtering smoke or plumes, filtering small particulate, filtering specific amounts of viruses or bacteria, reducing the amount of and/or killing viruses, bacteria, or fungi, or affecting allergenicity, collectively particulate P (purified air, purifying).

Referring again to FIGS. 1-6, in this embodiment face shield with powered air purifying respirator system 100 may have face shield 1 configured to shield the user's U face F and block small and large-particle droplets, splashes, sprays, or splatter (shield splatter) that may contain germs (viruses and bacteria) from entering the wearers eyes, nose, or mouth. Face shield 1 may be formed of or molded as a transparent or optically clear material and preferably formed or molded as an optically clear component and formed as a single uniform curve or a double curved clear component (FIG. 23) or pair of curved panels with center seam 1A to maximize visibility therethrough face shield 1. Face shield 1 may be configured to block small and large-particle droplets, splashes, sprays, or splatter (SP) that may contain germs (viruses and bacteria) from entering the wearers eyes E, nose N, or mouth M (shield splatter).

Face shield 1 may include face shroud 13 connected to shield perimeter 1B of face shield 1 and preferably formed or molded as an optically clear component. Moreover, face shroud 13 may be configured to provide a seal between the face shield and the user's U face F sides, chin C. Face shroud 13 may be configured to provide a seal between the face shield 1 and the user's U face F forming a seal around shroud perimeter 13A to block small and large-particle droplets, splashes, sprays, or splatter (SP) that may contain germs (viruses and bacteria) from entering the wearers eyes E, nose N, or mouth M around the side or shield perimeter 1.1 of face shield 1.

It is contemplated herein that face shield 1 may alternatively be made as a separate part from filter cowl 2, outer perimeter flange 8, and face shroud 13 (set forth below) in the event there is a desire to replace face shield 1 more often than the rest of the respirator due to scratches, etc. or if a higher grade of face shield protection is required such as for grinding applications.

It is contemplated herein that face shield 1 may be configured as a single horizontal curve with no vertical curve for ease of manufacturing, lowered manufacturing cost, and improved visualization.

Face shroud 13 may include fan housing, conduit, or filtered air chamber 4 configured as a bill or visor shape structure having a filter cowl 2, such as outer perimeter flange 8, having back perimeter flange edge 8A and visor and front perimeter flange edge 8B. Outer perimeter flange 8 may be configured to receive and hold in place exterior filter media 7 thereabout outer perimeter flange 8. The filter cowl 2 and outer perimeter flange 8 support the outer perimeter of the filter media 7 thus both maximizing or increasing the surface area (in square inches/centimeters) of the filter media while still keeping the overall profile of the respirator as minimal and as light weight as possible.

It is contemplated herein that face shroud 13 may be elastic to fit around a variety of user and/or may be air permeable to enable air to release from the mask area.

Face shroud 13 may be attached or connected to a perimeter of face shield 1 with face shroud 13 configured to provide a seal between face shield 1 and the user's face forming a seal around the perimeter of the respirator and the users face to block small and large-particle droplets, splashes, sprays, or splatter that may contain germs (viruses and bacteria) from entering the wearers eyes, nose, or mouth.

It is contemplated herein that face shroud 13 and structure 10 may be manufactured as a single piece for ease of manufacturing, lowered manufacturing cost, and improved visualization.

It is further contemplated herein that face shield 1, face shroud 13, and structure 10 may be combination pieces configured to be fitted together for ease of manufacturing, lowered manufacturing cost, cleaning and replaceability.

It is further contemplated herein that face shroud 13 may be configured with a curve forward to receive the bottom edge 1A of face shield 1 provide a seal between face shield 1 and the user's face (minimize gap between face shield 1 and wearer's chin C and enable face shield 1 to be configured as a single horizontal curve with no vertical curve for ease of manufacturing and improved visualization.

Face shroud 13 may be attached to the primary structure 10 via snap features, hook and loop systems, magnetic tape or other means. It is contemplated herein that filter cowl cover 14 may be part of face shroud 13 or a separate part.

It is contemplated herein that filtered air chamber 4 may have anti-reflective cowl treatment 17 such as preprinting or applying a secondary film to the localized area of the thermoformed sheet material with a flat black or other dark non reflective coating or film applied to filtered air chamber 4 and used to make the primary structure 10 or backside or underside of filtered air chamber 4 non reflective to reduce glare which can occur in the face shield 1 during use. Alternatively, filtered air chamber 4 may include a secondary formed part with the anti-reflective properties, masking under side of filtered air chamber 4 area and spraying anti-reflective coating, pad printing the under filtered air chamber 4 area of the formed part with anti-reflective coating, or dipping filtered air chamber 4 section of the primary structure 10 into an anti-reflective coating material.

It is further contemplated herein that optional permeable filter cowl cover 14 may be made of a breathable fabric that allows powered air purifying respirator system 100 to have an appearance that has less of a personal protective equipment look. This may be valuable to wearers in general public use scenarios when there is a wide spread pathogen concern or smoke or other poor air quality concern. Moreover, permeable filter cowl cover 14 may removeably attach to the primary structure 10 via snap features, hook and loop systems, magnetic tape or other means. Alternatively, both the permeable filter cowl cover 14 and face shroud 13 may be permanently attached through adhesives, thermally bonded, etc. for powered air purifying respirator system 100 designed to be a disposable product.

It is contemplated herein that filtered air chamber 4 or outer perimeter flange 8 may include one or more flange arch members extending across or bridging over filtered air chamber 4 to join two sides of outer perimeter flange 8 to support exterior filter media 7.

It is further contemplated herein that face shield with powered air purifying respirator system 100 components may be constructed as a single part which could be manufactured through a number of ways but would likely be either thermoformed from clear sheet material such as PETG, polycarbonate, acrylic, butyrate or injection molded with similar clear resins or high performance opaque materials for components not requiring transparency, as these material offers a variety of forms and shapes and provide strength with reduced weight; however, other suitable materials or the like, can be utilized, provided such material has sufficient strength and/or durability as would meet the purpose described herein to enable face shield with powered air purifying respirator system 100.

It is understood herein that various changes in the material used, shape, size, arrangement of parts, and parts are connected with bolts, pins, screws or similar fasteners or hinges or other rotating devices without departing from the spirit of the scope of the claims herein.

It is further understood herein that the parts and elements of this disclosure may be located or position elsewhere based on one of ordinary skill in the art without deviating from the present disclosure.

Exterior filter media 7 may include a filter media configured as two dimensional profile cut or flat shape, which may be fitted to outer perimeter flange 8 of the filter cowl 2 and an advantage to this configuration is that it provides a large surface area of filter media for filtering while not requiring any complex manufacturing forming operations as compared with other more complex filters, such as pleated media fitted into a cartridge, which reduces the filter cost and overall system cost. Thus, this filter design reduces the supply constraint issues, especially during high demand cycles during a pandemic and reduces the overall cost of the filter material and allows the greatest amount of flexibility in utilizing alternative filter media in emergency situations. Preferably, exterior filter media 7 is configured with straight back filter edge 7A and visor or bill shaped front filter edge 7B. An effective filter media may be capable of filtering smoke or plumes, filtering small particulate, filtering specific amounts of viruses or bacteria, reducing the amount of and/or killing viruses, bacteria, or fungi, or affecting allergenicity. Moreover, filter media may contain a coating technology to reduce and or kill microorganisms, may utilize nano- and micro-fiber layers for handling microscale droplets which evaporate into nanoscale aerosols carrying germs (viruses and bacteria).

It is contemplated herein that filter media 7 may be manufactured out of a number of different woven or non-woven types of filter media which may be mounted to outer perimeter flange 8 of the filter cowl 2.

It is contemplated herein that adhesive seal 9 may be utilized to seal filter media 7 to outer perimeter flange 8. Moreover, adhesive seal 9 may be integral to filter media 7 and used to adhere filter media 7 to outer perimeter flange 8. Moreover, adhesive seal 9 may include back adhesive seal edge 9A and front adhesive seal edge 9B.

It is further contemplated herein that filter media 7 covers a relatively large surface area and that there is significant volume in the filter chamber 4, and thus enables the possibility to install a pleated filter cartridge 38 or an activated carbon charcoal (or any specialized performance filter media) filter cartridge 39. Pleated filter cartridge 38 or filter cartridge 39 may utilize the same sealing approach to the filter media via the outer perimeter flange 8 if higher filtering performance is required. Pleated filter cartridge 38 may be constructed utilizing a pleated filter media potting seal 43 which would be molded around the pleated filter media 44 during production and this seal would interface in the same manner as the two dimensional filter media 7 does with the outer perimeter flange 8. Alternatively, activated charcoal filter cartridge 38 may be comprised of an activated carbon filter media layer 40 laminated between an air-permeable filter media layer 42 and the activated carbon filter three dimensional seal 41.

It is recognized herein that exterior filter media 7 enables filtering of air prior to entrance into filtered air chamber 4 rather than an interior filter which contaminates the internal passageways (filtered air chamber 4) prior to the filtration.

It is further recognized herein that exterior filter media 7 enables quick exchange and easy replacement of filter media since exterior filter media 7 is positioned on the exterior of powered air purifying respirator system 100 enabling use of a variety of filter material with nano- and micro-fiber layers to be utilize and enables frequent rotation of filter material always insuring a dry and bacteria, virus, and particle free filter material.

It is still further recognized herein that exterior filter media 7 provides an increased filter surface area to provide adequate air flow through the filter material to provide a positive air pressure proximate wearers eyes, nose, and mouth.

It is still further recognized herein that filter cowl perimeter flange 8 may be formed as a single ruled surface so that the filter media 7 and the adhesive seal 9 can be applied without the need of the distorting either into a 3rd dimension. It is envisioned that the adhesive seal 9 may be replaceable so that the wearer can change out the filter media 7 as needed. In this preferred embodiment it is envisioned that the adhesive seal 9 may be part of the filter media 7 and thus disposed of with the replaced filter media 7. It is envisioned that the new filter media 7 may have the adhesive seal 9 already adhered to the filter media and a backing film (not illustrated) would be removed from the filter media 7 exposing adhesive seal 9 which would be placed against the surface of the filter cowl 2, and perimeter flange 8. These features of filter cowl 2, outer perimeter flange 8, filter media 7, and adhesive seal 9 which make up powered air purifying respirator system 100 are designed to be moldable without the need for side action in the production tool with the possible exceptions of the fan support 3 hole features and for mounting provisions 35 to connect head strap 6. This novel approach reduces the cost and weight of powered air purifying respirator system 100.

An adhesive, or hook and loop, such as adhesive seal 9 (adhesive seal) may be adhered to outer perimeter flange 8 to enable quick replacement and exchange of exterior filter media 7. In one alternate embodiment, adhesive seal 9 may be bonded to exterior filter media 7 around filter perimeter 7C to enable quick replacement and exchange of exterior filter media 7. A feature of the present disclosure may include exterior filter media 7 configured having a removable adhesive backer to adhere and seal exterior filter media 7 to filter cowl, outer perimeter flange 8 may include one or more flange arch members extending across or bridging over fan conduit 3A, and outer perimeter flange 8.

Filtered air chamber 4 may be formed as a single mold or molded with an integral Face shield 1. Moreover, filtered air chamber 4 may include one wall as an inset, contour, or divot wall section to accommodate or fit a wearer's W forehead FH and allow powered air purifying respirator system 100 to rest on the forehead FH of wearer W. Furthermore, filtered air chamber 4 may include a contour, such as conduit well 4A to draw or gather filtered air to removeable motorized fan 11.

Moreover, filter housing, such as filtered air chamber 4 may include a slot, snap, such as mounting provisions 6 positioned on an upper left and right side of filtered air chamber 4 to enable releasably engagement of first strap end 34A and a second strap end 34B of strap 34 to secure adjustable strap 34 around wearer's W head H and removeably attach powered air purifying respirator system 100 to forehead FH of wearer W.

It is contemplated herein that first strap end 34.1 and a second strap end 34.2 of strap 34 may utilize attachment device to adjust the size of the strap and may be configured using hook and loop, clasp, slot, hook or other like attachment devices.

It is recognized herein that mounting provisions 6 may be utilized to mount powered air purifying respirator system 100 to head gear or helmet in contact with at least a portion of wear's head H.

Motorized fan 11 may include a single fan assembly or a plurality of fan assemblies removeably affixed to filtered air chamber 4. Referring again to FIG. 3, air flow AF are arrows illustrating the flow of air through powered air purifying respirator system 100. Motorized fan 11 may have an integral power supply or be powered by a remote power supply, such as a battery pack or rechargeable battery 22 on a belt or powered by solar panels or the like.

Preferably headgear battery mount 23 carries or supports rechargeable battery 22. Headgear battery mount 23 and the rechargeable battery 22 are mounted to headgear 34 towards the rear of the wearer's head so that the weight of these elements is counter balanced with the weight of the respirator.

Moreover, motorized fan 11 may be an axial fan assembly, which are commonly used in numerous products, particularly electronics, and thus are produced at very high production volumes which reduces the cost and offers advantages from a manufacturing procurement standpoint. The version shown is a standard 50×50 mm×10 mm thick configuration with 4 corner mounting holes. However, other fan designs such as radial or blower designs could be used. The motorized fan 11 may be powered via the power cord 12 which in this case is shown as a USB cord which can be plugged into standard battery modules which are readily available and used to generally power mobile phones and tablet devices. However, other electrical power systems could be used as well.

Another optional battery mount part may be utilized with motorized fan 11, such as fan isolation gasket 15, which provides both air sealing and some motorized fan 11 vibration dampening which primarily would serve to reduce noise generated by motorized fan 11. Fan fasteners 16 are illustrated as screws (four per motorized fan 11); however, it would be possible to use other fastening means such as rivets, heat staked posts, double sided adhesives, glues, and the like.

It is contemplated herein that filtered air chamber 4 may be molded into the primary structure 10.

It is contemplated herein that filtered air chamber 4 may include fan support 3, forehead support wall 5, and outer perimeter flange 8 to provide a fan plenum box for motorized fan 11 to enable efficient movement of airflow AF and to provide a large surface are for filter media 7.

The large arrow AF1 pointing at the top of exterior filter media 7 represents the unfiltered ambient air with suspended particulate P, the smaller arrows AF2 shown in filter chamber 4 represents the filtered air flow moving through fan conduit 3A to motorized fan 11. Exit air, the medium arrows AF3, represents the filtered air flow moving to wearer's W nose and mouth positioned between face shield 1 and face shroud 13, the filter airspace between the wearer's face F and the face shield 1. Smallest arrows AF4 at the bottom of face shield 1 and face shroud 13 disclose airflow exiting air permeable face shroud 13 and exiting powered air purifying respirator system 100, and thus, this produces a positive pressure condition in the space between wearer's face and face shield 1 and face shroud 13 which prevents the wearer from being exposed to the potentially contaminated ambient environment and blocks smoke or plumes, filtering small particulate, viruses or bacteria or fungi, or affecting allergenicity from gaining access to from entering the wearers eyes, nose, or mouth.

It is further contemplated herein that exterior filter media 7 is positioned exterior to filtered air chamber 4 and motorized fan 11 to filter large arrow AF1 before entry into filtered air chamber 4 and motorized fan 11 to maintain these areas free of a as maintain these areas contaminated ambient environment and blocks smoke or plumes, filtering small particulate, viruses or bacteria or fungi, or affecting allergenicity.

An elastic air permeable face shroud 13 may be an optional element to exiting powered air purifying respirator system 100. It is contemplated herein that exterior filter media 7, motorized fan 11, and face shield 1 without face shroud 13 may be configured where filtered air is blown into the space between the wearers face and the interior of the face shield. This produces a positive pressure condition which prevents the wearer from being exposed to the potentially contaminated ambient environment and blocks smoke or plumes, filtering small particulate, viruses or bacteria or fungi, or affecting allergenicity from gaining access to from entering the wearers eyes, nose, or mouth.

It is further contemplated herein that face shroud 13 may be utilized in industrial and medical use settings where face shroud 13 may prevent fast moving particles and debris generated by work such as cutting, grinding, sand blasting, lathe turning, etc. from overcoming the positive air pressure envelop produced by powered air purifying respirator system 100.

Referring again to FIGS. 7 and 8, powered air purifying respirator system 100 may include filter media compression vented cover 18, wherein vented cover 18, may be permeable having cover vents 19. Filter media compression vented cover 18 may be designed to provide compression to filter media 7 around the entire perimeter of the filter media 7 to outer perimeter flange 8 to enable quick replacement and exchange of exterior filter media 7. An optional filter media compressible gasket 29 may be utilized to enhance sealing between filter media 7 and outer perimeter flange 8. Optional filter media compressible gasket 29 may be either adhered or integrally molded to the outer perimeter flange 8 of primary structure 30 or to the filter media 7. Filter media compression vented cover 18 may be configured with cover flange 20 along the perimeter of the cover which may be utilized to secures filter media compression vented cover 18 to outer perimeter flange 8 of the primary structure 10/30. A cover snap latch 21 may be molded into the filter media compression vented cover 18 which enables a user or wearer W to release filter media compression vented cover 18 to quickly change the filter media 7.

Filter media compression vented cover 18 is shown with a plurality of cover vents 19 arranged along the front and up the side edges of the filter media compression vented cover 18 to enable air flow to filter media 7. It is contemplated herein that plurality of cover vents 19 may be formed with any number of venting slots, rigid screen material or permeable woven or non-woven materials.

It is contemplated herein that primary structure 30 is conceptually identical to primary structure 10 with the exception of some mounting details and fan openings and thus some of the feature descriptions for primary structure 10 are used to describe primary structure 30.

The large arrow AF1 pointing at plurality of cover vents 19 of filter media compression vented cover 18 and small arrow AF1A represents the unfiltered ambient air with suspended particulate P traversing over the filter media 7, the smaller arrows AF2 shown in fan conduit 3A represents the filtered air flow moving through fan conduit 3A to motorized fan 11. Exit air, the medium arrows AF3, represents the filtered air flow moving through fan diffuser 28 attached to the underside of motorized fan 11 and then to wearer's W nose and mouth positioned between face shield 1 and face shroud 13, the filter airspace between the wearer's face F and the face shield 1. Smallest arrows AF4 at the bottom of face shield 1 and face shroud 13 disclose airflow exiting air permeable face shroud 13 and exiting powered air purifying respirator system 100, and thus, this produces a positive pressure condition in the space between wearer's face and face shield 1 and face shroud 13 which prevents the wearer from being exposed to the potentially contaminated ambient environment and blocks smoke or plumes, filtering small particulate, viruses or bacteria or fungi, or affecting allergenicity from gaining access to enter the wearers eyes, nose, or mouth.

Referring now to FIGS. 9-13, by way of example, and not limitation, there is illustrated an example embodiment of fan and head gear assembly of face shield with powered air purifying respirator system 100A, according to this select embodiment. Face shield with powered air purifying respirator system 100A may be utilized as an air purifying respirator for a wearer W or user's head H having face F, forehead FH and back head BH with face shield 1 provide the functionality of filtering smoke or plumes, filtering small particulate, filtering specific amounts of viruses or bacteria, reducing the amount of and/or killing viruses, bacteria, or fungi, or affecting allergenicity, collectively particulate P.

Referring again to FIGS. 9-12, in this fan and head gear assembly embodiment of face shield with powered air purifying respirator system 100A may have face shield 1 configured to shield the wearer's W face F from block small and large-particle droplets, splashes, sprays, or splatter that may contain germs (viruses and bacteria) from entering the wearers eyes, nose, or mouth. Face shield 1 may be formed of or molded as a transparent or optically clear material and preferably formed or molded as an optically clear component and formed as a single uniform curve or pair of curved panels to maximize visibility therethrough face shield 1. Face shield 1 may be configured to block small and large-particle droplets, splashes, sprays, or splatter (SP) that may contain germs (viruses and bacteria) from entering the wearers eyes E, nose N, or mouth M.

Face shield 1 may include face shroud 13 connected to shield perimeter 1B of face shield 1 and preferably formed or molded as an optically clear component. Moreover, face shroud 13 may be configured to provide a seal between the face shield and the user's U face F sides, chin C. Face shroud 13 may be configured to provide a seal between the face shield 1 and the wearer's W face F forming a seal around shroud perimeter 13A to block small and large-particle droplets, splashes, sprays, or splatter (SP) that may contain germs (viruses and bacteria) from entering the wearers eyes E, nose N, or mouth M around the side or shield perimeter 1A of face shield 1.

It is contemplated herein that face shield 1 may alternatively be made as a separate part from filter cowl 2, outer perimeter flange 8, and face shroud 13 (set forth below) in the event there is a desire to replace face shield 1 more often than the rest of the respirator due to scratches, etc. or if a higher grade of face shield protection is required such as for grinding applications.

It is contemplated herein that face shield 1 may be configured as a single horizontal curve with no vertical curve for ease of manufacturing, lowered manufacturing cost, and improved visualization.

Face shroud 13 may include fan housing, conduit, or filtered air chamber 4 configured as a bill or visor shape structure having a filter cowl 2, such as outer perimeter flange 8. Fan housing, conduit, or filtered air chamber 4 may be configured as a bill or visor shape structure. Outer perimeter flange 8 may be configured to receive and hold in place exterior filter media 7 thereabout outer perimeter flange 8. The filter cowl 2 and outer perimeter flange 8 support the outer perimeter of the filter media 7 thus both maximizing the surface area of the filter media while still keeping the overall profile of the respirator as minimal and as light weight as possible.

Face shroud 13 may be attached or connected to a perimeter of face shield 1 with face shroud 13 configured to provide a seal between face shield 1 and the user's face forming a seal around the perimeter of the respirator and the users face to block small and large-particle droplets, splashes, sprays, or splatter that may contain germs (viruses and bacteria) from entering the wearers eyes, nose, or mouth.

It is contemplated herein that face shroud 13 and structure 30 may be manufactured as a single piece for ease of manufacturing, lowered manufacturing cost, and improved visualization.

It is further contemplated herein that face shield 1, face shroud 13, and structure 30 may be combination pieces configured to be fitted together for ease of manufacturing, lowered manufacturing cost, cleaning and replaceability.

It is further contemplated herein that face shroud 13 may configured with a curve forward to receive the bottom edge 1A of face shield 1 provide a seal between face shield 1 and the user's face (minimize gap between face shield 1 and wearer's chin C and enable face shield 1 to be configured as a single horizontal curve with no vertical curve for ease of manufacturing and improved visualization.

Face shroud 13 may be attached to the primary structure 30 via snap features, hook and loop systems, magnetic tape or other means. It is contemplated herein that filter cowl cover 14 may be part of face shroud 13 or a separate part.

It is contemplated herein that filtered air chamber 4 may have anti-reflective cowl treatment 17 such as preprinting or applying a secondary film to the localized area of the thermoformed sheet material with a flat black or other dark non reflective coating or film applied to filtered air chamber 4 and used to make the primary structure 30 or backside or underside of filtered air chamber 4 non reflective to reduce glare which can occur in the face shield 1 during use. Alternatively, filtered air chamber 4 may include a secondary formed part with the anti-reflective properties, masking under side of filtered air chamber 4 area and spraying anti-reflective coating, pad printing the under filtered air chamber 4 area of the formed part with anti-reflective coating, or dipping filtered air chamber 4 section of the primary structure 30 into an anti-reflective coating material.

It is further contemplated herein that optional permeable filter cowl cover 14 may be made of a breathable fabric that allows powered air purifying respirator system 100A to have an appearance that has less of a personal protective equipment look. This may be valuable to wearers in general public use scenarios when there is a wide spread pathogen concern or smoke or other poor air quality concern. Moreover, permeable filter cowl cover 14 may removeably attach to the primary structure 30 via snap features, hook and loop systems, magnetic tape or other means. Alternatively, both the permeable filter cowl cover 14 and face shroud 13 may be permanently attached through adhesives, thermally bonded, etc. for powered air purifying respirator system 100A designed to be a disposable product.

It is contemplated herein that filtered air chamber 4 or outer perimeter flange 8 may include one or more flange arch members extending across or bridging over filtered air chamber 4 to join two sides of outer perimeter flange 8 to support exterior filter media 7.

It is further contemplated herein that face shield with powered air purifying respirator system 100A components may be constructed as a single part which could be manufactured through a number of ways but would likely be either thermoformed from clear sheet material such as PETG, polycarbonate, acrylic, butyrate or injection molded with similar clear resins or more specifically high density polyethylene or similar high tensile or strengthened materials, as these material offers a variety of forms and shapes and provide strength with reduced weight; however, other suitable materials or the like, can be utilized, provided such material has sufficient strength and/or durability as would meet the purpose described herein to enable face shield with powered air purifying respirator system 100A to be unfolded into a chaise lounge.

It is understood herein that various changes in the material used, shape, size, arrangement of parts, and parts are connected with bolts, pins, screws or similar fasteners or hinges or other rotating devices without departing from the spirit of the scope of the claims herein.

It is further understood herein that the parts and elements of this disclosure may be located or position elsewhere based on one of ordinary skill in the art without deviating from the present disclosure.

Exterior filter media 7 may include a filter media configured as two dimensional flat shape which may be fitted to outer perimeter flange 8 of the filter cowl 2 and an advantage to this configuration is that it provides a large surface area of filter media for filtering while not requiring any complex manufacturing forming operations as compared with other more complex filters, such as pleated media fitted into a cartridge, which reduces the filter cost and overall system cost. Thus, this filter design reduces the supply constraint issues, especially during high demand cycles during a pandemic and reduces the overall cost of the filter material and allows the greatest amount of flexibility in utilizing alternative filter media in emergency situations. Preferably, exterior filter media 7 is configured with straight back filter edge 7A and visor or bill shaped front filter edge 7B. An effective filter media may be capable of filtering smoke or plumes, filtering small particulate, filtering specific amounts of viruses or bacteria, reducing the amount of and/or killing viruses, bacteria, or fungi, or affecting allergenicity. Moreover, filter media may contain a coating technology to reduce and or kill microorganisms, may utilize nano- and micro-fiber layers for handling microscale droplets which evaporate into nanoscale aerosols carrying germs (viruses and bacteria).

It is contemplated herein that filter media 7 may be manufactured out of a number of different woven or non-woven types of filter media which may be mounted to outer perimeter flange 8 of the filter cowl 2.

It is further contemplated herein that filter media 7 covers a relatively large surface area and that there is significant volume in the filter chamber 4, and thus enables the possibility to install a pleated filter cartridge 38 or an activated carbon charcoal (or any specialized performance filter media) filter cartridge 39. Pleated filter cartridge 38 or filter cartridge 39 may utilize the same sealing approach to the filter media via the outer perimeter flange 8 if higher filtering performance is required. Pleated filter cartridge 38 may be constructed utilizing a pleated filter media potting seal 43 which would be molded around the pleated filter media 44 during production and this seal would interface in the same manner as the two dimensional filter media 7 does with the outer perimeter flange 8. Alternatively, activated charcoal filter cartridge 38 may be comprised of an activated carbon filter media layer 40 laminated between an air-permeable filter media layer 42 and the activated carbon filter three dimensional seal 41.

It is recognized herein that exterior filter media 7 enables filtering of air prior to entrance into filtered air chamber 4 rather than an interior filter which contaminates the internal passageways (filtered air chamber 4) prior to the filtration.

It is further recognized herein that exterior filter media 7 enables quick exchange and easy replacement of filter media since exterior filter media 7 is positioned on the exterior of powered air purifying respirator system 100A enabling use of a variety of filter material with nano- and micro-fiber layers to be utilize and enables frequent rotation of filter material always insuring a dry and bacteria, virus, and particle free filter material.

It is still further recognized herein that exterior filter media 7 provides an increased filter surface area to provide adequate air flow through the filter material to provide a positive air pressure proximate wearers eyes, nose, and mouth.

It is still further recognized herein that filter cowl perimeter flange 8 may be formed as a single ruled surface so that the filter media 7 and the adhesive seal 9 can be applied without the need of the distorting either into a 3rd dimension. It is envisioned that the adhesive seal 9 may be replaceable so that the wearer can change out the filter media 7 as needed. In this preferred embodiment it is envisioned that the adhesive seal 9 may be part of the filter media 7 and thus disposed of with the replaced filter media 7. It is envisioned that the new filter media 7 may have the adhesive seal 9 already adhered to the filter media and a backing film (not illustrated) would be removed from the filter media 7 exposing adhesive seal 9 which would be placed against the surface of the filter cowl 2, and perimeter flange 8. These features of filter cowl 2, outer perimeter flange 8, filter media 7, and adhesive seal 9 which make up powered air purifying respirator system 100A are designed to be moldable without the need for side action in the production tool with the possible exceptions of the dual fan support 3 hole features and for mounting provisions 35 to connect head strap 6. This novel approach reduces the cost and weight of powered air purifying respirator system 100A.

An adhesive, or hook and loop, such as adhesive seal 9 may be adhered to outer perimeter flange 8 to enable quick replacement and exchange of exterior filter media 7. In one alternate embodiment, adhesive seal 9 may be bonded to exterior filter media 7 around filter perimeter 7C to enable quick replacement and exchange of exterior filter media 7. A feature of the present disclosure may include exterior filter media 7 configured having a removable adhesive backer to adhere and seal exterior filter media 7 to filter cowl, outer perimeter flange 8 may include one or more flange arch members extending across or bridging over fan conduit 3A, and outer perimeter flange 8.

Filtered air chamber 4 may be formed as a single mold or molded with an integral face shield 1 to receive fan diffuser assembly 24 configured to be separable therefrom face shield 1. Moreover, filtered air chamber 4 may include one wall as an inset, contoured, or divot wall section, such as forehead support wall 5 to accommodate a wearer's W forehead FH and allow powered air purifying respirator system 100A to rest on the forehead FH of wearer W. Furthermore, filtered air chamber 4 may include a contour, such as conduit well 4A to draw or gather filtered air to removeable motorized fan 11.

Moreover, fan diffuser assembly 24 may include a slot, snap, such as mounting provisions 35 positioned on left and right (first and second) back end of diffuser assembly 24 to enable releasably engagement or connect first strap end 34A and a second strap end 34B of strap 34 to secure strap 34 around wearer's W head H and removeably attach powered air purifying respirator system 100A to forehead FH of wearer W.

It is contemplated herein that first strap end 34A and a second strap end 34B of strap 34 may utilize attachment device to adjust the size of the strap and may be configured using hook and loop, clasp, slot, hook or other like attachment devices.

It is recognized herein that mounting provisions 35 may be utilized to mount powered air purifying respirator system 100A to head gear or helmet in contact with at least a portion of wear's head H.

In this second preferred embodiment, fan diffuser assembly 24 carries the dual or two motorized fans 11, such as first motorized fan 11A and second motorized fan 11B via fan diffuser frame 25 which has latch assembly 26 and assembly tab 27 formed as bill shaped to insert therein, inset motion IM, where latch assembly 26 latches to mounting tab slot 32 which secures fan diffuser assembly 24 to primary structure 30 having bill shaped cavity in a slide and latch motion. In this embodiment, the dual or two motorized fans 11, such as first motorized fan 11A and second motorized fan 11B, are smaller than the fan in the first embodiment (FIGS. 1-8) at 40×40×10 mm but together move the same CFM of air. This arrangement provides a more compact design and thus closer spacing between the face shield 1 and the wearer's face.

Moreover, latch assembly 26 and assembly tab 27 engage with mounting provision 31 and mounting tab slot 32 which are both features of primary structure 30 having bill shaped cavity for a slide and latch motion to secure fan diffuser assembly 24 therein primary structure 30 having bill shaped cavity. Ideally, the diffuser frame 25 would be molded in a flat black or other non-glare inducing surface.

Dual motorized fan 11A/11B may have an integral power supply or be powered by a remote power supply, such as a battery pack or rechargeable battery 22 on a belt or powered by solar panels or the like.

In this second preferred embodiment, fan diffuser assembly 24 may include diffuser frame 25 designed in a similar manner as the primary structures 10 and 30 and this design can be manufactured with few side action or secondary processes during the production process. One or more fan diffuser 28 may be formed integral to the fan diffuser frame 25 or as a separate piece. Fan diffuser fasteners 16 are illustrated as screws (four per fan diffuser 24) to mount fan diffuser 24, compression gasket 33, and motorized fan 11 to fan diffuser frame 25, each respectively; however, it would be possible to use other fastening means such as rivets, heat staked posts, double sided adhesives, glues, and the like.

Fan diffuser frame 25 may be utilized to redirect filtered air from at least one motorized fans 11, or from first motorized fan 11A and second motorized fan 11B, such as slightly towards the face shield 1 to avoid the wearer W having more direct air flow shown in the first preferred embodiment. It is contemplated herein that fan diffuser 28 may be rotational to enable redirection of filtered air from at least one motorized fans 11, or from first motorized fan 11A and second motorized fan 11B, in any direction between face shield1 and face shroud 13.

It is contemplated herein that fan filter assembly 24 may be inserted and latched therein primary structure 30.

It is contemplated herein that filtered air chamber 4 may include fan support 3, forehead support wall 5, and outer perimeter flange 8 to provide a fan plenum box for dual motorized fans 11 to enable efficient movement of airflow AF and to provide a large surface are for filter media 7.

An optional arrangement has an auxiliary fan diffuser duct 45 which redirects a small percent of filtered air from at least one motorized fans 11, or from first motorized fan 11A and second motorized fan 11B, towards the wearer's W forehead FH to provide cooling of wearer's W forehead FH and thus improved comfort. This auxiliary fan diffuser duct 45 can be used with an optional forehead cushion 46. Forehead cushion 46 is preferably formed of a porous material, such as open celled polyurethane foam to allow cooling air dispersion through the contact surfaces of forehead cushion 46.

The large arrow AF1 pointing at plurality of cover vents 19 of filter media compression vented cover 18 and small arrow AF1A represents the unfiltered ambient air with suspended particulate P traversing over the filter media 7, the smaller arrows AF2 shown in fan conduit 4 represents the filtered air flow moving through filtered air chamber 4 to dual motorized fan 11A/11B. Exit air, through fan diffuser duct 28 and 45 the medium arrows AF3, represents the filtered air flow moving or is diverted in two directions, direction 1-AF3A) a portion of dual motorized fan 11A/11B output towards the wearer's W forehead FH via forehead cushion 46, and direction 2-AF3B) the remainder of dual motorized fan 11A/11B output toward wearer's W nose and mouth positioned between face shield 1 and face shroud 13, the filter airspace between the wearer's face F and the face shield 1, and thus, this produces a positive pressure condition in the space between wearer's face and face shield 1 and face shroud 13 which prevents the wearer from being exposed to the potentially contaminated ambient environment and blocks smoke or plumes, filtering small particulate, viruses or bacteria or fungi, or affecting allergenicity from gaining access to enter the wearers eyes, nose, or mouth.

Preferably headgear battery mount 23 carries or supports rechargeable battery 22. Headgear battery mount 23 and the rechargeable battery 22 are mounted to headgear 34 towards the rear of the wearer's head so that the weight of these elements is counter balanced with the weight of the respirator.

Moreover, dual motorized fan 11A/11B may be an axial fan assembly, which are commonly used in numerous products, particularly electronics, and thus are produced at very high production volumes which reduces the cost and offers advantages from a manufacturing procurement standpoint. However, other fan designs such as radial or blower designs could be used. Dual motorized fan 11A/11B may be powered via the power cord 12 which in this case is shown as a USB cord which can be plugged into standard battery modules which are readily available and used to generally power mobile phones and tablet devices. However, other electrical power systems could be used as well.

Another optional battery mount part may be utilized with dual motorized fan 11A/11B, such as compression gasket 33 as a single assembly or a pair of compression gasket, such as first compression gasket 33A and second compression gasket 33B as separate individual compression gasket, which provides a seal between dual motorized fan 11A/11B, between fan diffusers, such as first fan diffuser 28A and second fan diffuser 28B and fan support 3 of the filter chamber 4, and also provides vibration dampening which primarily would serve to reduce noise generated by dual motorized fan 11A/11B.

An optional compression gasket 33 assures a seal between the motorized fans 11 and the fan support 3 of the filter chamber 4 which are features of the primary structure 30.

It is contemplated herein that filtered air chamber 4 may be molded into the primary structure 30 with dual mounting provision 3A formed therein support 3 as apertures therethrough to mate up with and support fan diffuser duct 28 and 45 and dual motorized fan 11A/11B, respectively.

It is further contemplated herein that exterior filter media 7 is positioned exterior to filtered air chamber 4 and dual motorized fan 11A/11B to filter large arrow AF1 before entry into filtered air chamber 4 and dual motorized fan 11A/11B to maintain these areas free of and maintain these areas contaminated ambient environment and blocks smoke or plumes, filtering small particulate, viruses or bacteria or fungi, or affecting allergenicity.

An elastic air permeable face shroud 13 may be an optional element to exiting powered air purifying respirator system 100A. It is contemplated herein that exterior filter media 7, dual motorized fan 11A/11B, and face shield 1 without face shroud 13 may be configured where filtered air is blown into the space between the wearers face and the interior of the face shield. This produces a positive pressure condition which prevents the wearer from being exposed to the potentially contaminated ambient environment and blocks smoke or plumes, filtering small particulate, viruses or bacteria or fungi, or affecting allergenicity from gaining access to from entering the wearers eyes, nose, or mouth.

It is further contemplated herein that face shroud 13 may be utilized in industrial and medical use settings where face shroud 13 may prevent fast moving particles and debris generated by work such as cutting, grinding, sand blasting, lathe turning, etc. from overcoming the positive air pressure envelop produced by powered air purifying respirator system 100A.

Figure 11:
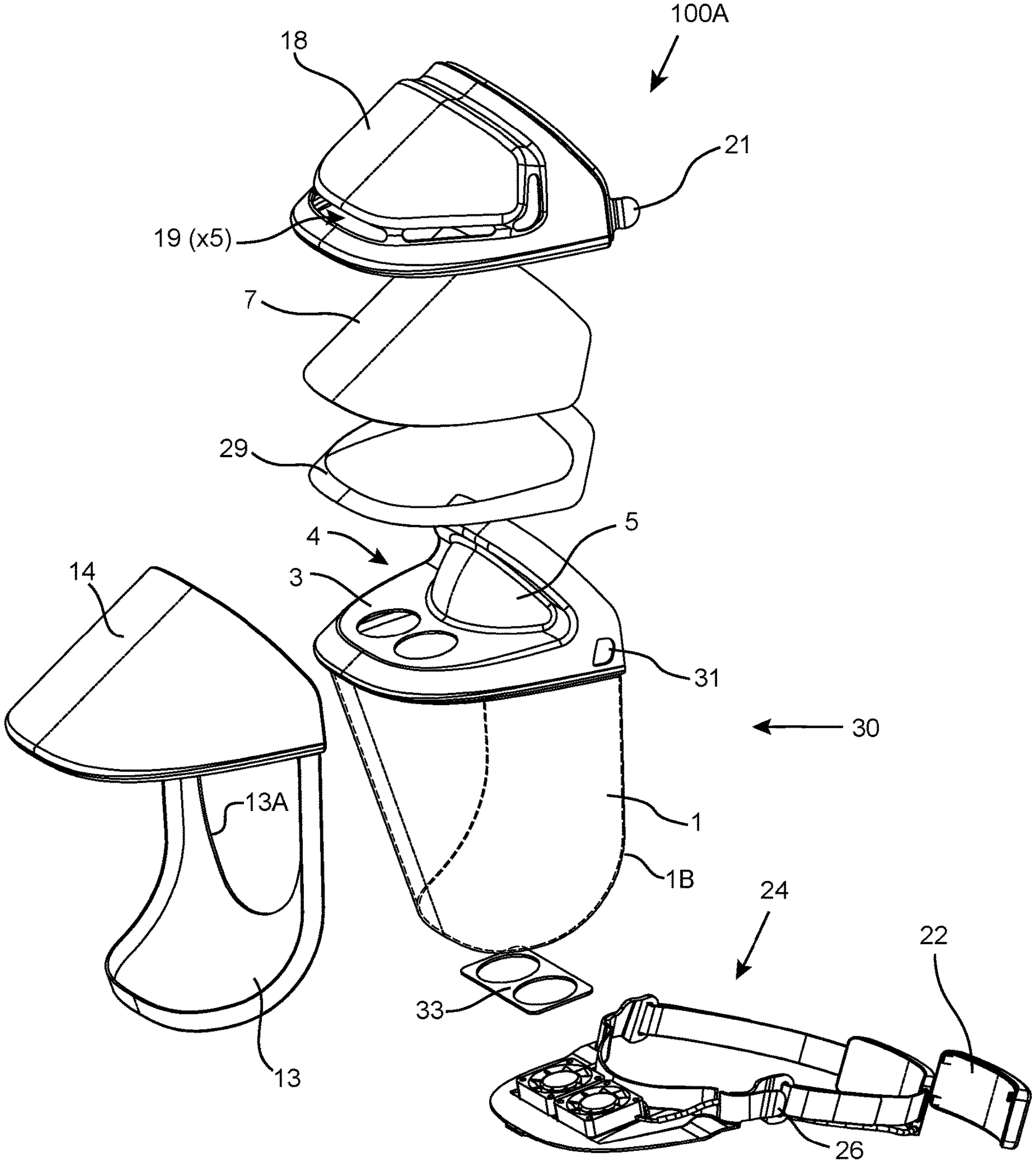
FIG. 11 is an exploded perspective view of the powered air purifying respirator system according to select embodiments of the instant disclosure set forth in FIGS. 9 and 10.
Figure 12:
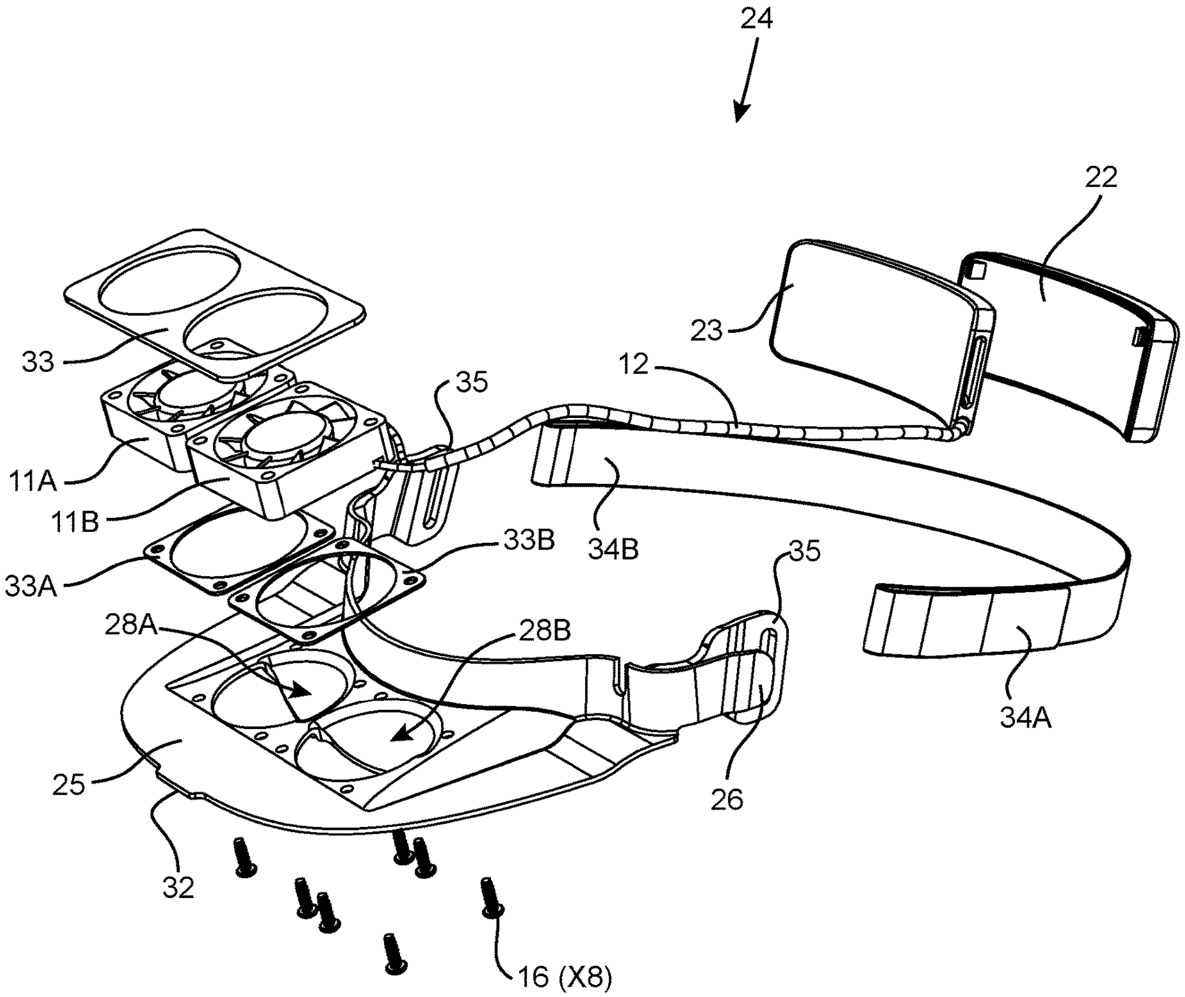
FIG. 12 is an exploded perspective view of the fan diffuser frame, fan diffuser, fan, and headgear powered air purifying respirator system according to select embodiments of the instant disclosure set forth in FIGS. 9 and 10.
Figure 13:
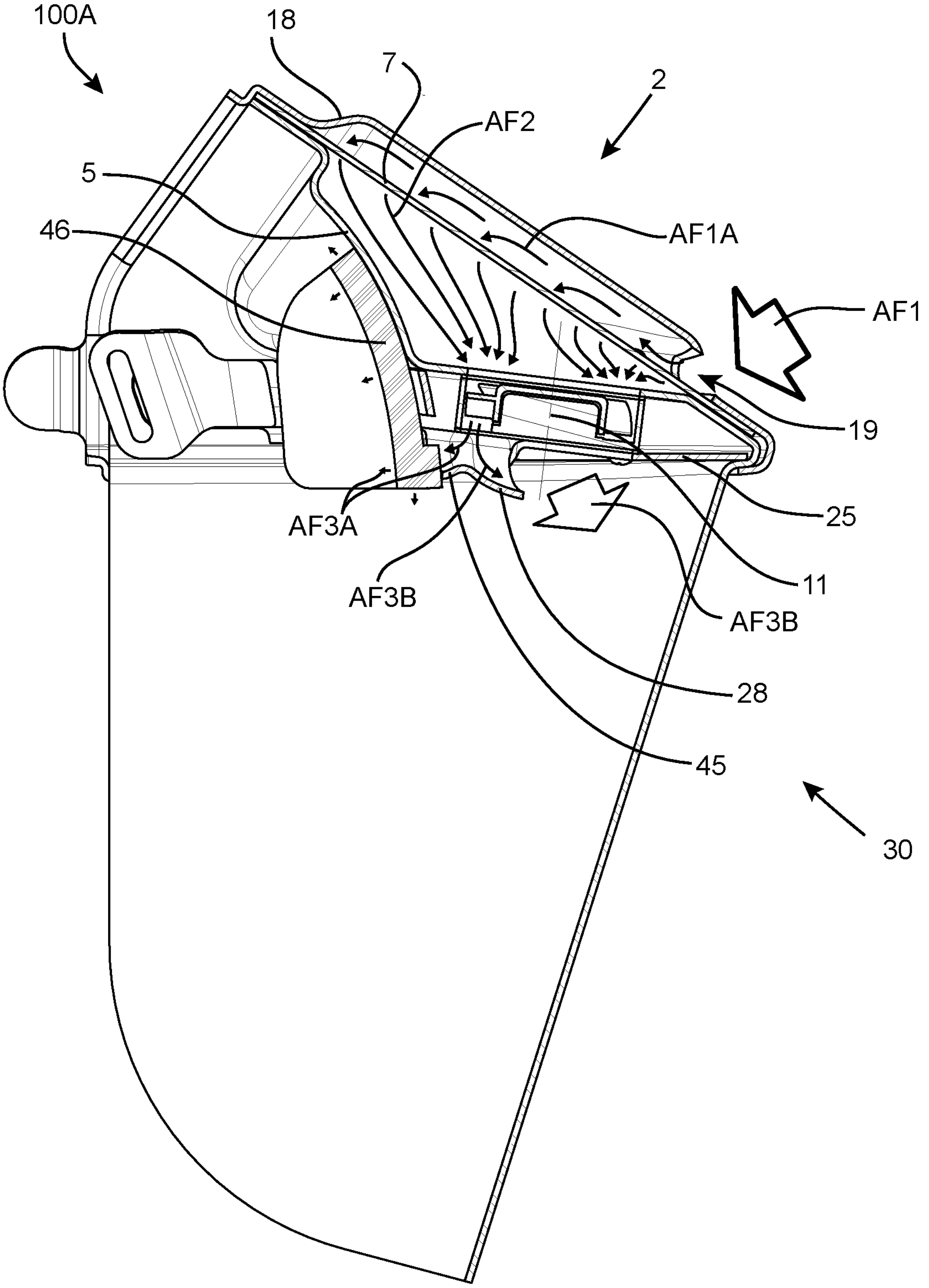
FIG. 13 is a partial cross-sectional side view of the powered air purifying respirator system according to select embodiments of the instant disclosure in FIGS. 9-12, showing air flow patterns through the vented cover, filter material, fan, and into the area between the face shield and wearer's face and foam cushion.

Referring to FIG. 11, powered air purifying respirator system 100A may include filter media compression vented cover 18. Filter media compression vented cover 18 may be designed to provide compression to filter media 7 around the entire perimeter of the filter media 7 to outer perimeter flange 8 to enable quick replacement and exchange of exterior filter media 7. An optional filter media compressible gasket 29 may be utilized to enhance sealing between filter media 7 and outer perimeter flange 8. Optional filter media compressible gasket 29 may be either adhered or integrally molded to the outer perimeter flange 8 of primary structure 30 or to the filter media 7. Filter media compression vented cover 18 may be configured with cover flange 20 along the perimeter of the cover which may be utilized to secures filter media compression vented cover 18 to outer perimeter flange 8 of the primary structure 10/30. A cover snap latch 21 may be molded into the filter media compression vented cover 18 which enables a user or wearer W to release filter media compression vented cover 18 to quickly change the filter media 7.

Filter media compression vented cover 18 is shown with a plurality of cover vents 19 arranged along the front and up the side edges of the filter media compression vented cover 18 to enable air flow to filter media 7. It is contemplated herein that plurality of cover vents 19 may be formed with any number of venting slots, rigid screen material or permeable woven or non-woven materials.

It is contemplated herein that primary structure 30 is conceptually identical to primary structure 10 with the exception of some mounting details and fan openings and thus some of the feature descriptions for primary structure 10 are used to describe primary structure 30.

The large arrow AF1 pointing at plurality of cover vents 19 of filter media compression vented cover 18 and small arrow AF1A represents the unfiltered ambient air with suspended particulate P traversing over the filter media 7, the smaller arrows AF2 shown in filtered air chamber 4 represents the filtered air flow moving through fan conduit 5 to dual motorized fan 11A/11B. Exit air, the medium arrows AF3, represents the filtered air flow moving to wearer's W nose N and mouth M positioned between face shield 1 and optional face shroud 13, the filter airspace between the wearer's face F and the face shield 1. Smallest arrows AF4 at the bottom of face shield 1 and face shroud 13 disclose airflow exiting air permeable face shroud 13 and exiting powered air purifying respirator system 100, and thus, this produces a positive pressure condition in the space between wearer's face and face shield 1 and face shroud 13 which prevents the wearer from being exposed to the potentially contaminated ambient environment and blocks smoke or plumes, filtering small particulate, viruses or bacteria or fungi, or affecting allergenicity from gaining access to enter the wearers eyes, nose, or mouth.

Referring again to FIG. 14, face shield 1 may be integrated with welders helmet to form powered air purifying respirator system 100B. Powered air purifying respirator system 100B may be configured replacing primary structure 10, 30 and face shield 1 with welding shield 36. Welding shield 36 is nontransparent material to block welding sparks and flashes on a trajectory toward wearer's face F. Moreover, welding shield 36 may be configured with a lens aperture 36A configured to removeably secure therein welding lens 37 to enable welder to visualize welding while wearing powered air purifying respirator system 100B. Otherwise powered air purifying respirator system 100B may include the other features listed above in FIGS. 1-13.

It is contemplated herein that fan filter assembly 24 may be inserted and latched therein primary structure 30B.

It is further contemplated herein that fan filter assembly 24 may provide cool air flow to wearer's W face F between welding shield 36 and wearer's W face F via fan filter assembly 24.

It is still further contemplated herein that fan filter assembly 24, filter media 7 may provide a positive pressure condition in the space between wearer's face and face shield 1 and face shroud 13 which prevents the wearer from being exposed to the potentially contaminated ambient environment and blocks smoke or plumes, filtering small particulate, viruses or bacteria or fungi, or affecting allergenicity from gaining access to enter the wearers eyes, nose, or mouth.

It is recognized herein that fan filter assembly 24 and headgear 34 may include a swivel or rotation connection for mounting provisions 35 to enable wearer W to tilt welding shield 36 between welding view (tilted down) and inspection or alignment view (tilted up).

Figure 14:
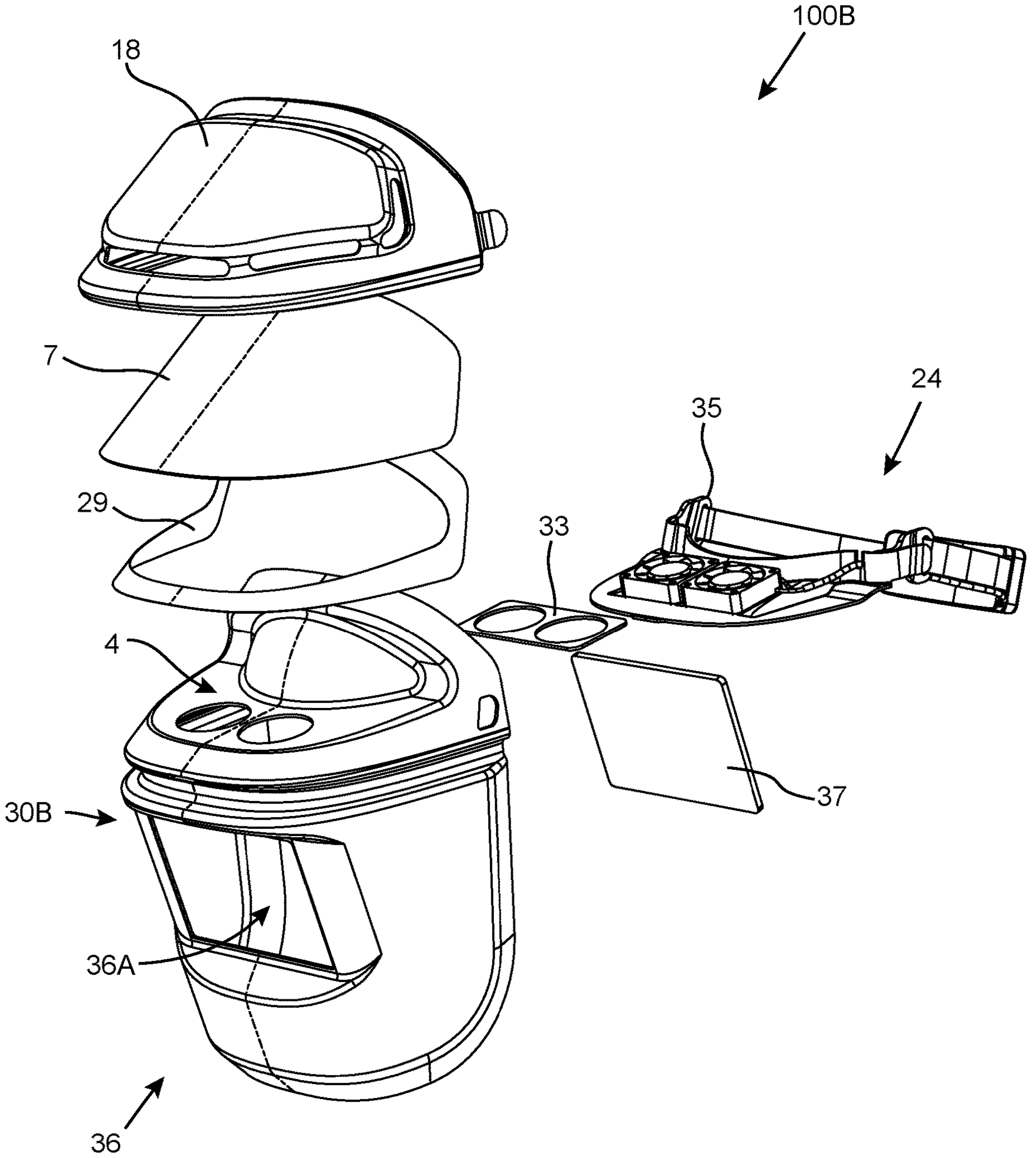
FIG. 14 is an exploded perspective view of the powered air purifying respirator system according to select embodiments of the instant disclosure, shown integratable with a welders helmet.

It is recognized herein that powered air purifying respirator system 100B with welding shield 36 may include filter media compression gasket 29, filter media 7, filter media compression vented cover 18, as shown in FIG. 14.

Figure 15:
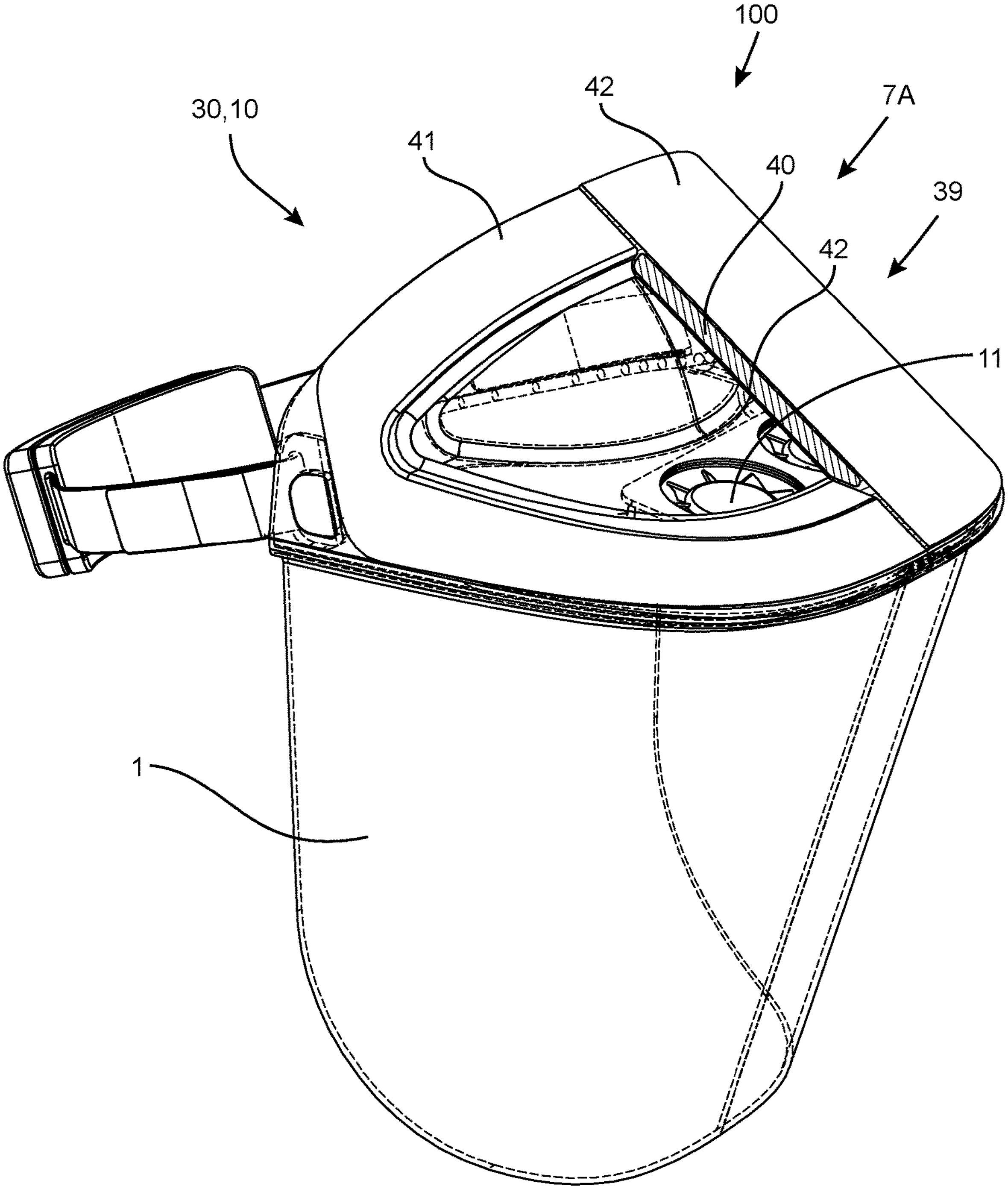
FIG. 15 is a perspective front side cutaway view of an alternate embodiment filter media of powered air purifying respirator system according to another select embodiment of the instant disclosure.
Figure 16:
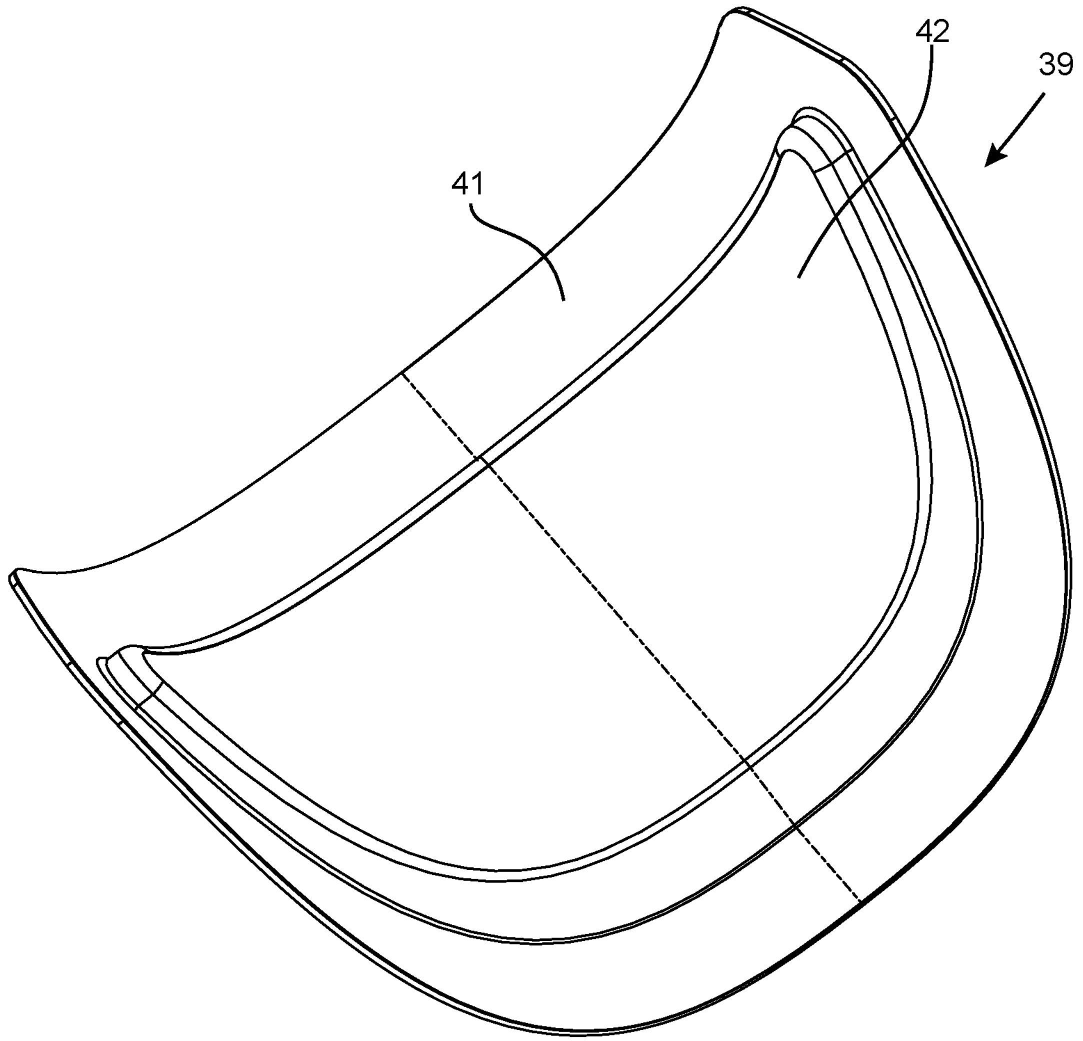
FIG. 16 is a perspective bottom view of an alternate embodiment gasket or seal of powered air purifying respirator system according to another select embodiment of the instant disclosure.

Referring to FIGS. 15 and 16, structure 10/30 may be integrated with a variety of filter media 7 for powered air purifying respirator system 100, such as activated charcoal filter cartridge 39. Powered air purifying respirator system 100 may be configured with activated charcoal filter cartridge 39, 7A that integrates filter media air permeable filter media layer 42 and activated carbon filter media layer 40. Activated carbon filter media layer 40 may include a filter layer with granular activated carbon (GAC), which is a proven option to remove certain chemicals, particularly organic chemicals, chemicals that give objectionable odors or tastes, and other harmful contaminants or allergens, minimizing potential health hazards.

It is contemplated herein that activated charcoal filter cartridge 39 may be integrated with powered air purifying respirator system 100 as a replacement for filter media 7.

Moreover, activated charcoal filter cartridge 39 may include activated carbon filter three dimensional seal 41, which may be utilized to enhance sealing between activated charcoal filter cartridge 39 and outer perimeter flange 8 of structure 10/30. Optional activated carbon filter three dimensional seal 41 may be either adhered or integrally molded to the outer perimeter flange 8 of primary structure 10/30 or to activated charcoal filter cartridge 39 for quick change of activated charcoal filter cartridge 39.

Alternatively, activated charcoal filter cartridge 38 may be configured of an activated carbon filter media layer 40 laminated between an air-permeable filter media layer 42 and the activated carbon filter three dimensional seal 41.

Figure 17:
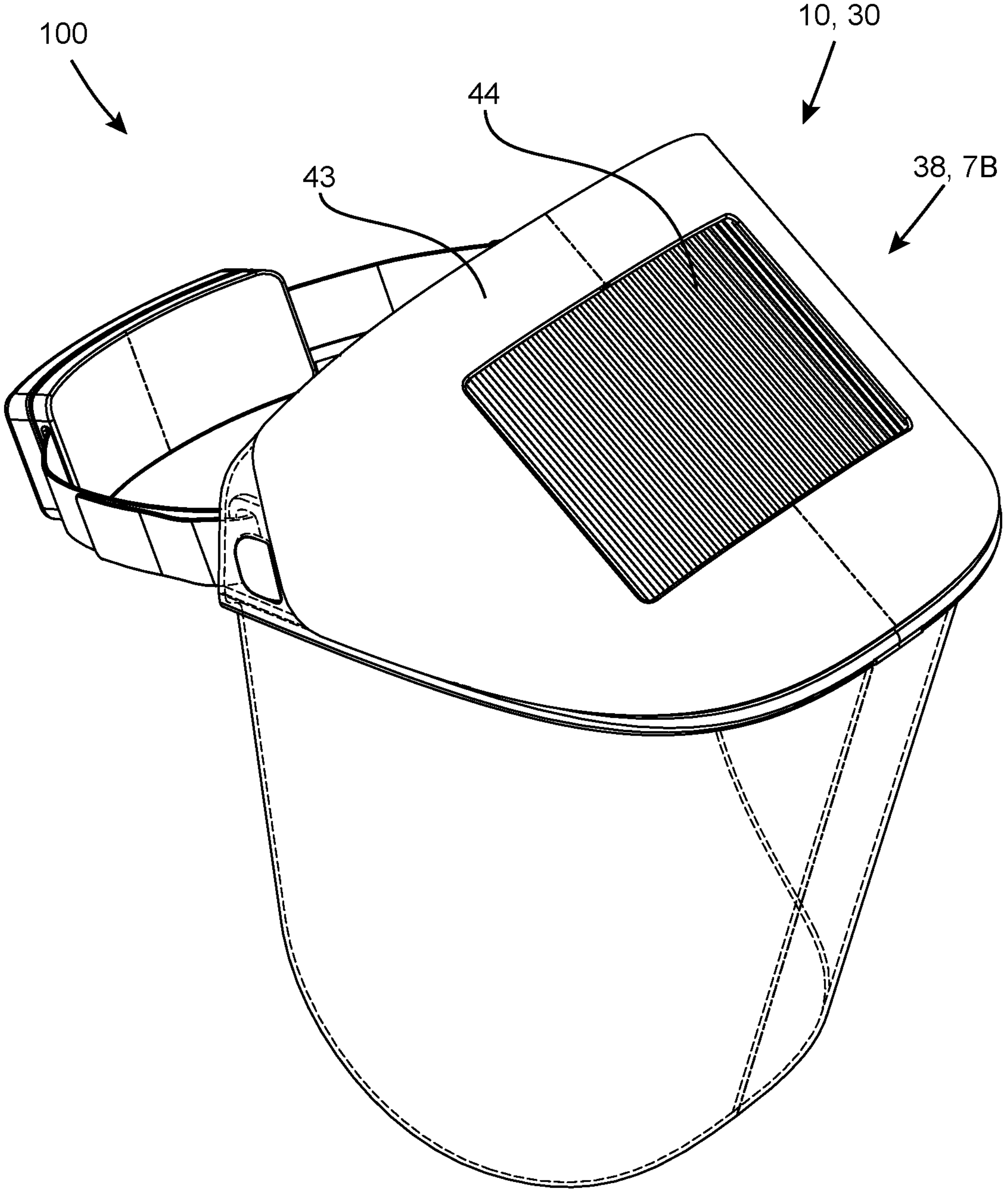
FIG. 17 is a perspective front side view of powered air purifying respirator system according to another select embodiment of the instant disclosure, showing an alternate embodiment filter media.
Figure 18:
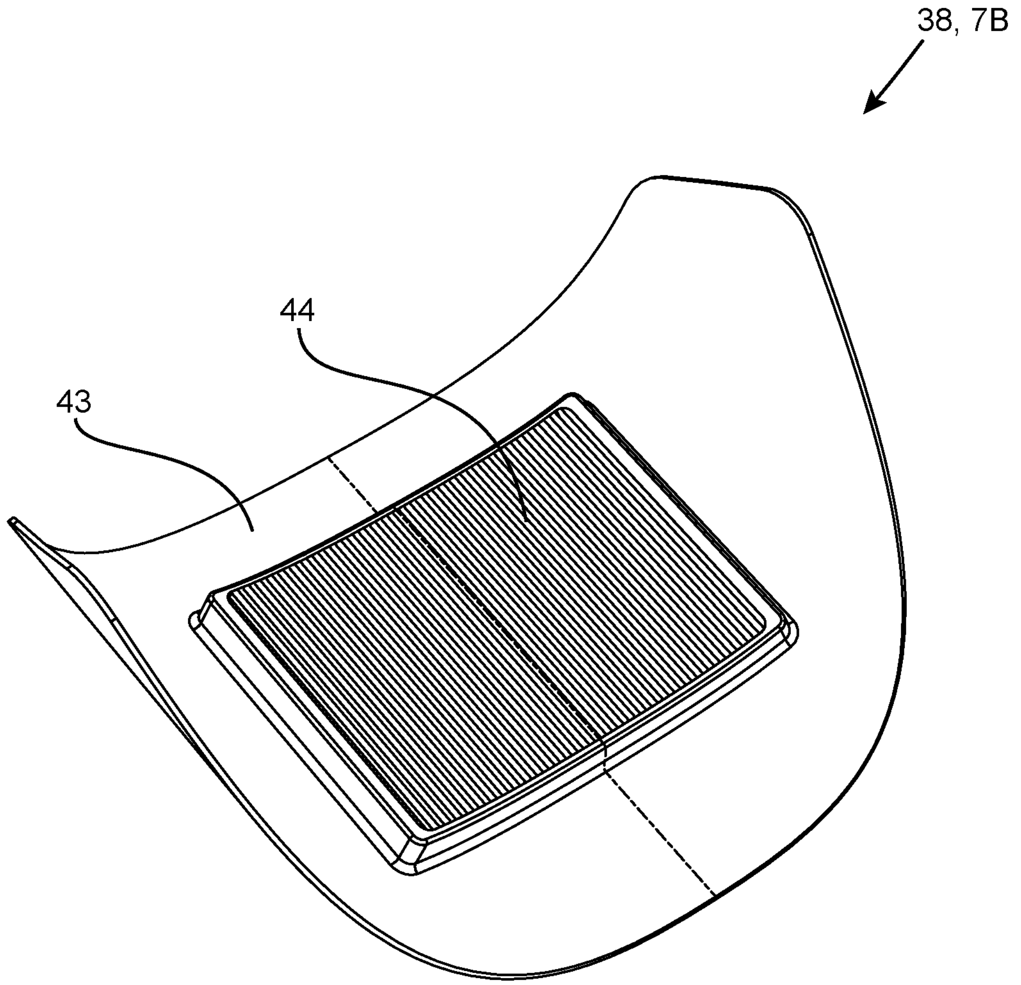
FIG. 18 is a perspective bottom side view of an alternate embodiment filter media according to another select embodiment of the instant disclosure.
Figure 19:
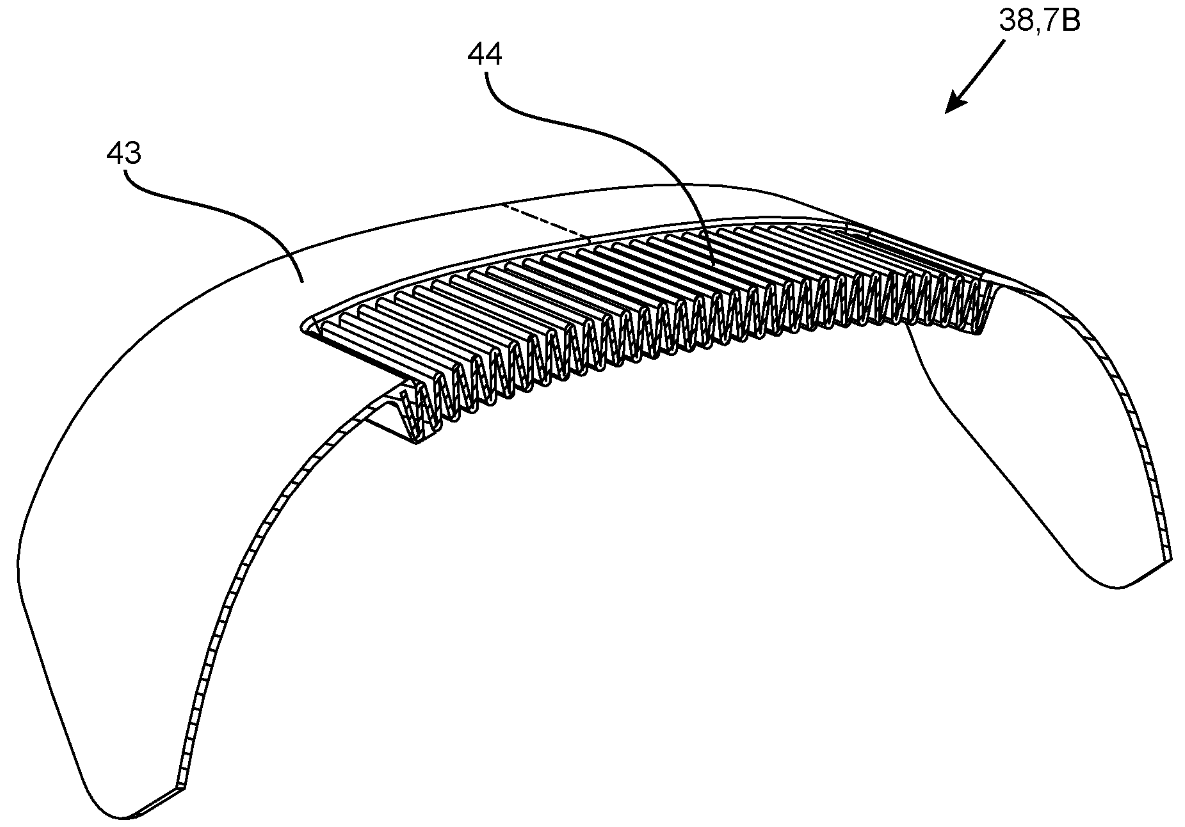
FIG. 19 is a cross-sectional view of an alternate embodiment filter media according to another select embodiment of the instant disclosure.

Referring to FIGS. 17, 18 and 19, structure 10/30 may be integrated with a variety of filter media 7B for powered air purifying respirator system 100, such as pleated filter media cartridge 38. Powered air purifying respirator system 100 may be configured pleated filter media cartridge 38, 7B that integrates pleated filter media 44 and pleated filter three dimensional seal 43. Pleated filter media cartridge 38 may be configured with the filter media in a folding pattern, which enables the filter media to have additional surface area for filtering more particles, such as potentially contaminated ambient environment and blocks smoke or plumes, filtering small particulate, viruses or bacteria or fungi, or affecting allergenicity from gaining access to enter the wearers eyes, nose, or mouth.

It is contemplated herein that pleated filter media cartridge 38 may be integrated with powered air purifying respirator system 100 as a replacement for filter media 7.

It is further contemplated herein that pleated filter cartridge 38 may utilize the same sealing approach to the filter media via the outer perimeter flange 8 if higher filtering performance is required. Pleated filter cartridge 38 may be constructed utilizing a pleated filter media potting seal 43 which would be molded around the pleated filter media 44 during production and this seal would interface in the same manner as the two dimensional filter media 7 does with the outer perimeter flange 8.

Moreover, pleated filter media cartridge 38 may include pleated filter three dimensional seal 43, which may be utilized to enhance sealing between configured pleated filter media cartridge 38 and outer perimeter flange 8 of structure 10/30. Optional pleated filter three dimensional seal 43 may be either adhered or integrally molded to the outer perimeter flange 8 of primary structure 10/30 or to pleated filter media cartridge 38 for quick change of activated charcoal filter cartridge 39.

Figure 20:
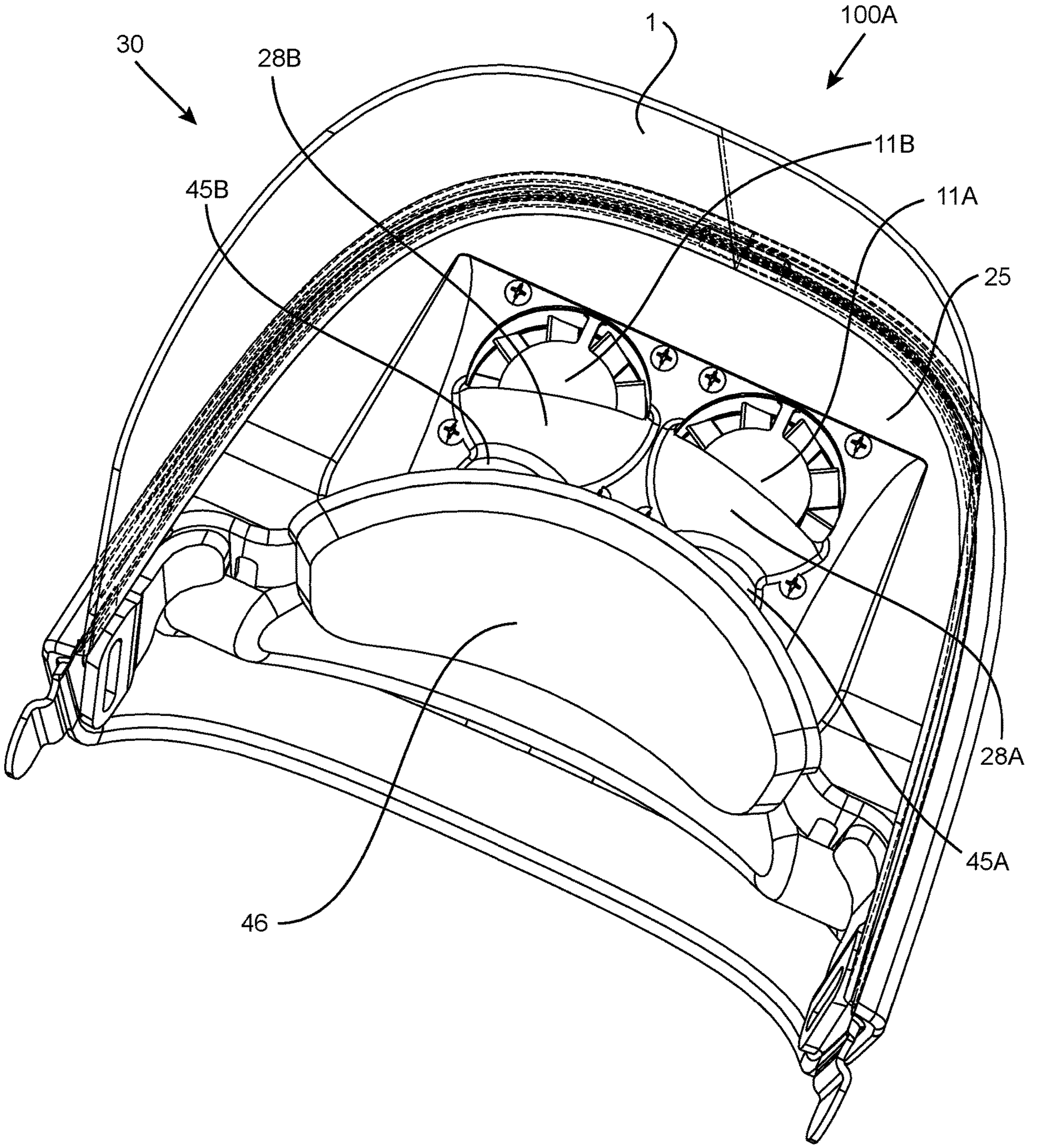
FIG. 20 is a bottom perspective view of the face shield, primary structure, fan assembly and forehead cushion of powered air purifying respirator system according to select embodiments of the instant disclosure.
Figure 21:
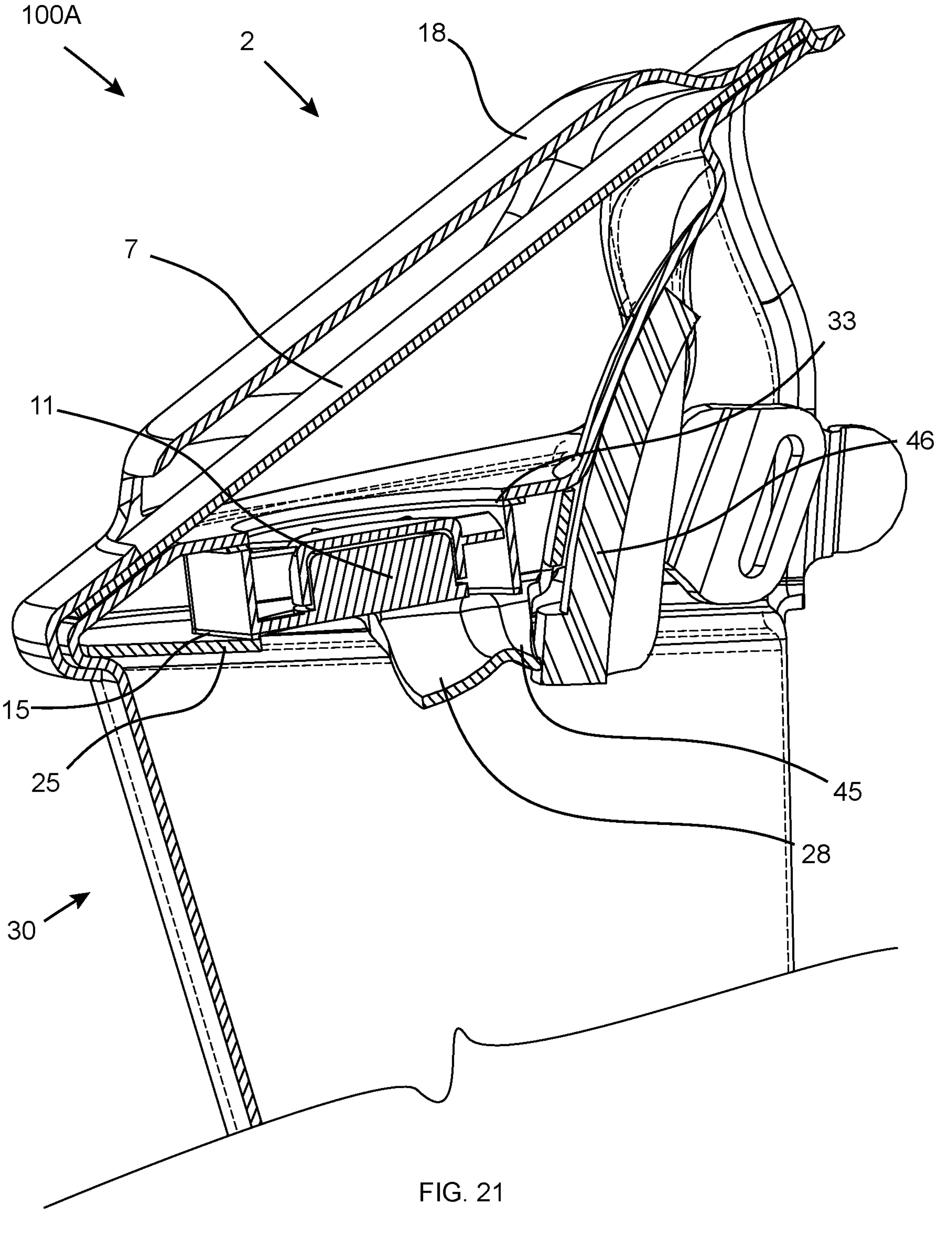
FIG. 21 is a partial cross-sectional side view of the powered air purifying respirator system according to select embodiments of the instant disclosure in FIGS. 9-12, 19, and 20, showing internal fan diffuser, auxiliary fan diffuser, duct for forehead cooling, and forehead cushion.
Figure 22:
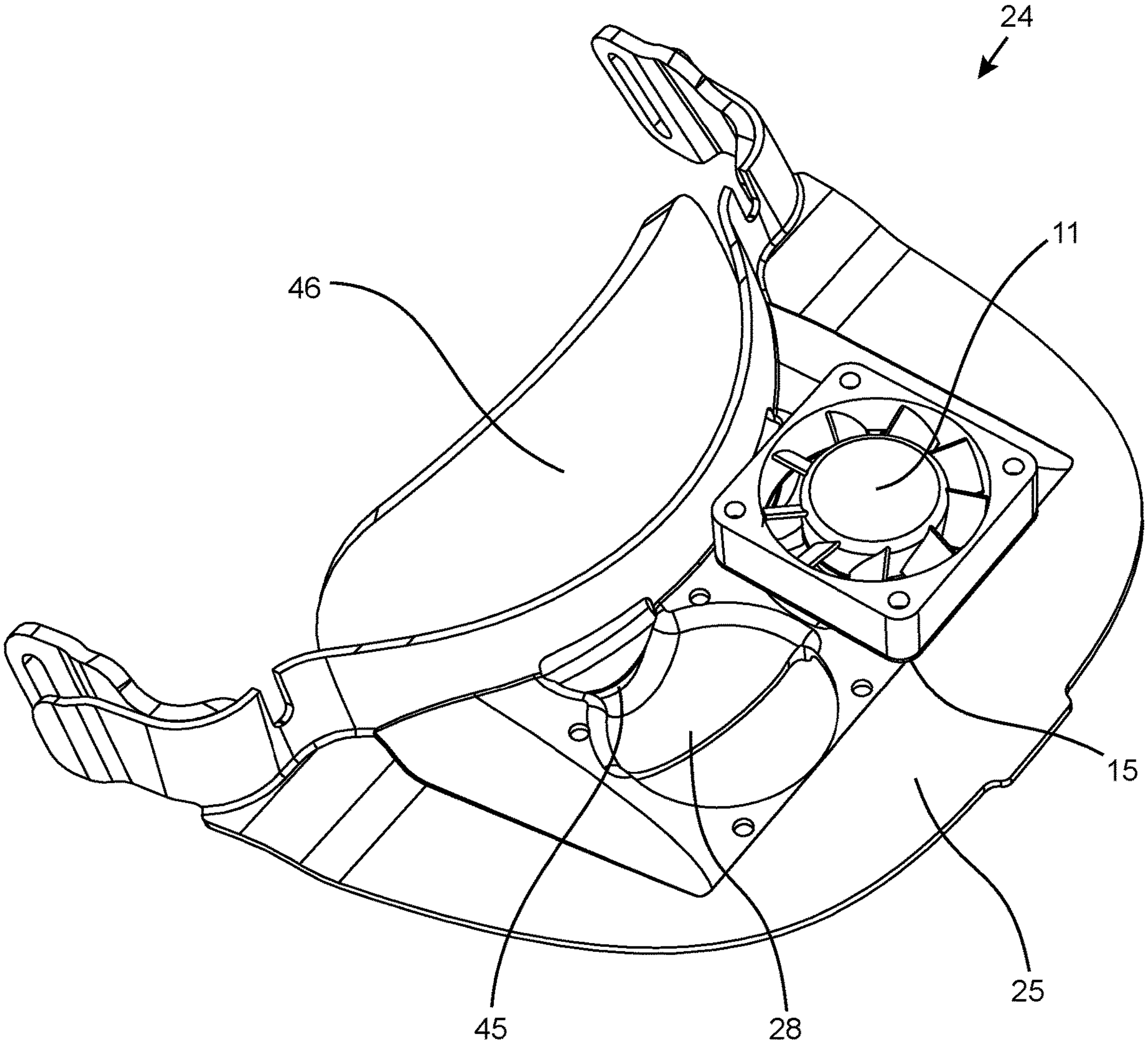
FIG. 22 is a top perspective view of the fan diffuser assembly and forehead cushion of the powered air purifying respirator system according to select embodiments of the instant disclosure.

Referring again to FIGS. 9-13, and now to FIGS. 20-22, powered air purifying respirator system 100A may have face shield 1, dual motorized fan 11A/11B configured in fan diffuser frame 25, with each fan pushing or blowing filtered air through fan diffusers, such as first fan diffuser 28A and second fan diffuser 28B which directs air flow AF3B between wearer's W face F and face shield 1 and auxiliary fan diffuser duct 45 which redirects a small percent of filtered air AF3A towards the wearer's W forehead FH to provide cooling of wearer's W forehead FH and thus improved comfort. This auxiliary fan diffuser duct 45 can be used with an optional forehead cushion 46. Forehead cushion 46 is preferably formed of a porous material, such as polyurethane foam to allow cooling air dispersion through the contact surfaces of forehead cushion 46.

Accordingly, in another aspect, the present disclosure may be configured where air is drawn through the filter media located on the outer brow area of the face shield via a motorized fan mounted between the filter media and above the plane of the eye brow of the wearer.

Accordingly, in another aspect, the present disclosure may be configured where filtered air is blown into the space between the wearers face and the interior of the face shield. This produces a positive pressure condition which prevents the wearer from being exposed to the potentially contaminated ambient environment the wearer is in.

Accordingly, in another aspect, the present disclosure may be configured where this barrier allows air to vent through the shroud but can serve to filter the wearer's exhalation and thus potential pathogens before exhausting into the environment. In applications where exhalation filtering isn't required this shroud can also protect the wearer from flying dust and debris which in some cases could overpower the positive pressure envelope as well as protecting side or back splashes, sprays, or splatter.

Figure 23:
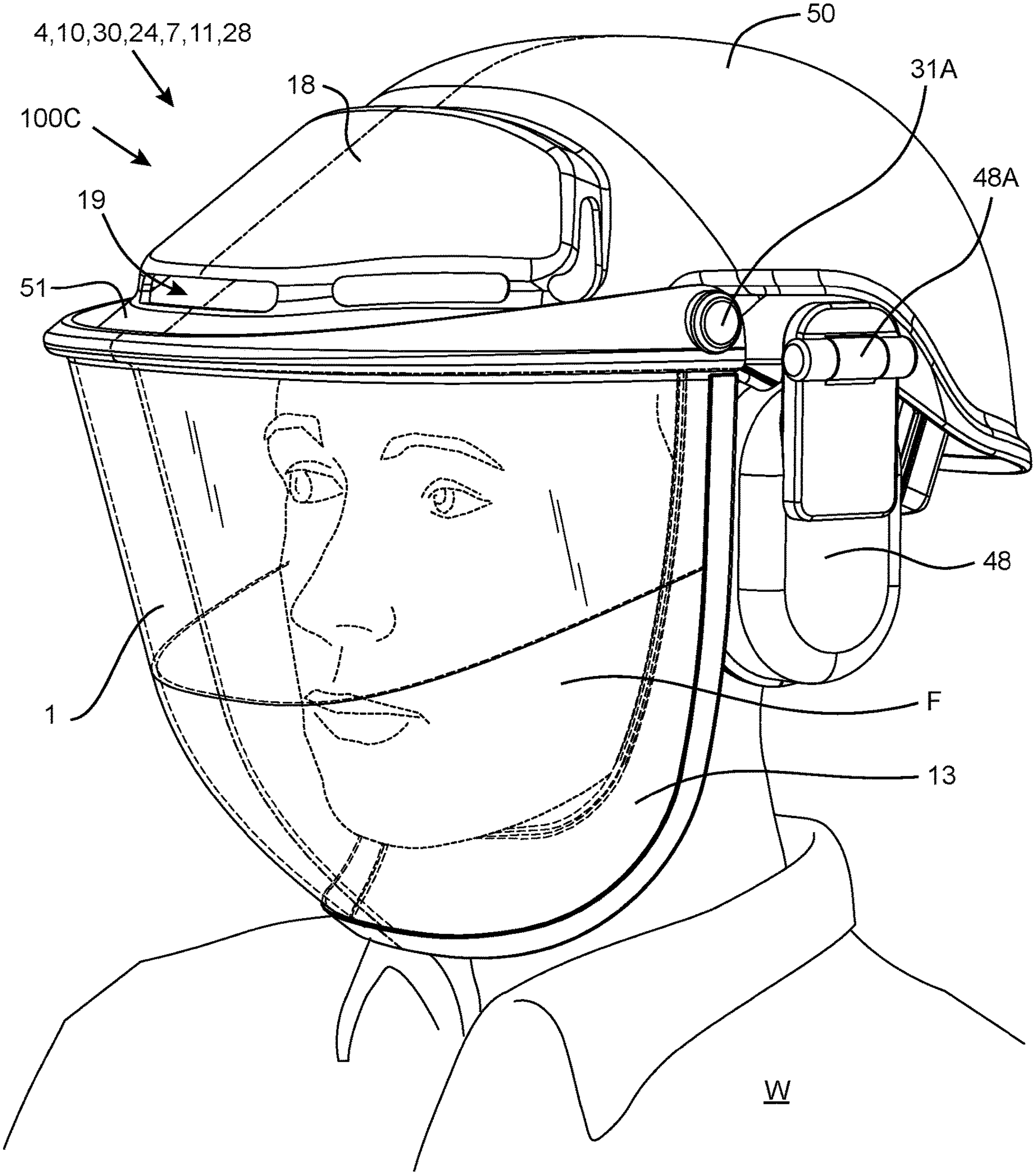
FIG. 23 is a perspective side view of the powered air purifying respirator system according to select embodiments of the instant disclosure, shown in use and worn by a wearer or user with the addition of hardhat.

Referring now to FIG. 23, in this fan and head gear assembly embodiment of face shield with powered air purifying respirator system 100C may have face shield 1 configured with a double ruled surface, face shroud 13, filter media compression vented cover 18 with cover vents 19 covering primary structure 10/30, filter chamber 4 with fan filter assembly 24 having fan diffuser 28, motorized fan 11, pulling air through filter media 7 as described above in FIGS. 1-22. In this embodiment, powered air purifying respirator system 100C may be integrated or removeably affixed to hardhat 50 or hardhat visor 51 and may alternatively be pivot affixed to hardhat 50 by mounting provision 31A to enable tilt up and down of powered air purifying respirator system 100C about mounting provision 31A and hardhat 50. In addition, hardhat 50 may include hearing protection 48 affixed to hardhat 50 to provide noise reduction hearing protection to wearer W. Hearing protection 48 may include pivotable mounting provision 48A to enable pivot up and down of hearing protection 48 to enable hearing protection when down and conversing with hearing protection pivoted in the up direction.

It is contemplated herein that powered air purifying respirator system 100C may be integrated or affixed to other types of headwear.

With respect to the above description then, it is to be realized that the optimum dimensional relationships, to include variations in size, materials, shape, form, position, movement mechanisms, function and manner of operation, assembly and use, are intended to be encompassed by the present disclosure.

The foregoing description and drawings comprise illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Moreover, the present disclosure has been described in detail, it should be understood that various changes, substitutions and alterations can be made thereto without departing from the spirit and scope of the disclosure as defined by the appended claims. Accordingly, the present disclosure is not limited to the specific embodiments illustrated herein but is limited only by the following claims.

The invention claimed is:

1. An air purifying respirator for a user's head having a face and a forehead to deliver a filtered air and provide shield to a splatter, said respirator comprising:

a face shield, said face shield configured to shield the user's face from the splatter;

a powered air purifying system, said system having at least one fan configured to provide a positive air pressure between said face shield and the user's face;

a fan housing positioned proximate an upper edge of said face shield, said fan housing having a fan support, a forehead support wall, a filter cowl having an outer perimeter flange formed as a single ruled surface, said outer perimeter flange having a front perimeter flange edge configured as a visor and an arched back perimeter flange edge positioned back and above said front perimeter flange edge, said front perimeter flange edge configured to support said fan internally therein and to enable efficient movement of the air;

a head strap attached to said fan housing, said head strap configured to encircle at least a portion of the users head, said head strap configured to support said fan housing; and a filter media configured as a two-dimensional planar profile, said filter media adapted to be fitted to said outer perimeter flange of said filter cowl to provide a large visor shape surface area of said filter media, while providing a minimum of an overall size of the air purifying respirator;

wherein said fan pulls the air through said filter media, and said fan is configured to push the filtered air from said fan housing to between said face shield and the user's face as said positive air pressure.

2. The respirator of claim 1, further comprising a face shroud connected to a perimeter of said face shield, said face shroud configured to provide a seal between said face shield and the user's face.

3. The respirator of claim 2, wherein said face shroud is configured as elastic to fit around the user's face.

4. The respirator of claim 2, wherein said face shroud is configured as air permeable to allow filtered air to exit, thereby maintaining the positive air pressure between said face shield and the user's face.

5. The respirator of claim 2, wherein said fan pulls air through said filter media into said fan housing, and said fan pushes said filtered air to the user between said face shield and said face shroud.

6. The respirator of claim 1, wherein said filter media, said at least one fan, and said fan housing are configured to deliver a positive pressure of the filtered air between said face shield and the user's face.

7. The respirator of claim 1, wherein said face shield is configured as a single horizontal curve to maximize visibility.

8. The respirator of claim 1, wherein said fan housing is configured as a visor shape.

9. The respirator of claim 1, wherein said head strap is adjustable in length about said fan housing.

10. The respirator of claim 1, further comprising a permeable filter cover, said permeable filter cover is positioned over said filter media and removeably attach to said outer perimeter flange and configured to compress said filter media against said outer perimeter flange to enhance sealing.

11. The respirator of claim 1, wherein said fan housing is contoured on one side to accommodate the forehead of the user.

12. The respirator of claim 11, further comprising a fan diffuser duct configured to direct a portion of the filtered air toward the user's forehead to provide cooling.

13. The respirator of claim 12, wherein said fan housing is configured with a forehead cushion.

14. The respirator of claim 13, wherein said forehead cushion is air permeable, said forehead cushion is configured to receive said portion of the filtered air.

15. The respirator of claim 1, further comprising an adhesive seal affixed to said filter media to removeably attach said filter media to said outer perimeter flange of said filter cowl.

16. The respirator of claim 1, wherein said fan housing further comprising a mounting provision to releasably connect said head strap thereto.

17. The respirator of claim 1, further comprising a power cord connected to said fan.

18. The respirator of claim 17, further comprising a battery mount affixed to said head strap, said battery mount configured to secure a battery thereto and connect to said power cord.

19. The respirator of claim 1, wherein said fan, said fan housing, and said head strap are configured to be separable therefrom said face shield.

20. The respirator of claim 1, wherein said face shield is formed of a transparent material.

21. The respirator of claim 1, wherein said face shield is formed of a nontransparent material.

22. The respirator of claim 21, wherein said face shield further comprising a welding lens configured therein.

23. An air purifying respirator for a user's head having a face and a forehead to deliver a filtered air and provide shield to a splatter, said respirator comprising:

a hard hat having a visor;

a powered air purifying system positioned proximate said visor, said system having a face shield, said face shield configured to shield the user's face from the splatter;

at least one fan configured to provide a positive air pressure between said face shield and the user's face;

a fan housing positioned proximate an upper edge of said face shield, said fan housing having a fan support, a forehead support wall, a filter cowl having an outer perimeter flange formed as a single ruled surface, said outer perimeter flange having a front perimeter flange edge configured as said visor and an arched back perimeter flange edge positioned back and above said front perimeter flange edge, said front perimeter flange edge and said back perimeter flange edge together form an outer perimeter flange, front perimeter flange edge configured to support said fan internally therein and to enable efficient movement of the air; and a filter media configured as a two-dimensional planar profile, said filter media adapted to be fitted to said outer perimeter flange of said filter cowl to provide a large visor shape surface area of said filter media, while providing a minimum of an overall size of the air purifying respirator;

wherein said fan pulls the air through said filter media, and said fan is configured to push the filtered air from said fan housing to between said face shield and the user's face as said positive air pressure.

24. The air purifying respirator of claim 23, wherein said fan housing is pivotably affixed to said hard hat to enable tilting of said face shield between an operational position and an inspection position.

* * * * *